US008383578B2

(12) United States Patent
Levetan et al.

(10) Patent No.: US 8,383,578 B2
(45) Date of Patent: *Feb. 26, 2013

(54) PEPTIDES, DERIVATIVES AND ANALOGS THEREOF, AND METHODS OF USING SAME

(75) Inventors: Claresa S. Levetan, Rosemont, PA (US); Loraine V. Upham, Albuquerque, NM (US)

(73) Assignee: CureDM Group Holdings, LLC, Wilmington, DE (US)

( * ) Notice: Subject to any disclaimer, the term of this patent is extended or adjusted under 35 U.S.C. 154(b) by 4 days.

This patent is subject to a terminal disclaimer.

(21) Appl. No.: 13/168,461

(22) Filed: Jun. 24, 2011

(65) Prior Publication Data
US 2011/0280833 A1 Nov. 17, 2011

Related U.S. Application Data

(60) Continuation of application No. 12/635,053, filed on Dec. 10, 2009, now Pat. No. 7,989,415, which is a division of application No. 12/121,123, filed on May 15, 2008, now Pat. No. 7,714,103, which is a continuation of application No. 11/441,491, filed on May 25, 2006, now Pat. No. 7,393,919.

(60) Provisional application No. 60/684,819, filed on May 25, 2005.

(51) Int. Cl.
A61K 38/00 (2006.01)
A61K 38/04 (2006.01)
A61K 51/00 (2006.01)
A01N 37/18 (2006.01)

(52) U.S. Cl. .................. 514/1.1; 530/326; 424/1.69

(58) Field of Classification Search .................. None
See application file for complete search history.

(56) References Cited

U.S. PATENT DOCUMENTS

| | | |
|---|---|---|
| 4,444,887 A | 4/1984 | Hoffmann |
| 4,716,111 A | 12/1987 | Osband et al. |
| 4,757,060 A | 7/1988 | Lukacsko et al. |
| 4,816,397 A | 3/1989 | Boss et al. |
| 4,816,567 A | 3/1989 | Cabilly et al. |
| 5,223,409 A | 6/1993 | Ladner et al. |
| 5,225,539 A | 7/1993 | Winter |
| 5,403,484 A | 4/1995 | Ladner et al. |
| 5,427,908 A | 6/1995 | Dower et al. |
| 5,436,169 A * | 7/1995 | Iovanna et al. ............... 436/518 |
| 5,516,637 A | 5/1996 | Huang et al. |
| 5,530,101 A | 6/1996 | Queen et al. |
| 5,565,332 A | 10/1996 | Hoogenboom et al. |
| 5,571,698 A | 11/1996 | Ladner et al. |
| 5,580,717 A | 12/1996 | Dower et al. |
| 5,580,859 A | 12/1996 | Felgner et al. |
| 5,585,089 A | 12/1996 | Queen et al. |
| 5,631,224 A | 5/1997 | Efendic et al. |
| 5,658,727 A | 8/1997 | Barbas et al. |
| 5,698,426 A | 12/1997 | Huse |
| 5,733,743 A | 3/1998 | Johnson et al. |
| 5,750,753 A | 5/1998 | Kimae et al. |
| 5,766,886 A | 6/1998 | Studnicka et al. |
| 5,780,225 A | 7/1998 | Wigler et al. |
| 5,807,715 A | 9/1998 | Morrison et al. |
| 5,821,047 A | 10/1998 | Garrard et al. |
| 5,834,590 A | 11/1998 | Vinik et al. |
| 5,840,531 A | 11/1998 | Vinik et al. |
| 5,959,086 A | 9/1999 | Iovanna et al. |
| 5,969,108 A | 10/1999 | McCafferty et al. |
| 6,311,415 B1 | 11/2001 | Lind |
| 6,407,213 B1 | 6/2002 | Carter et al. |
| 6,645,934 B1 | 11/2003 | Rodemann et al. |
| 6,946,151 B2 | 9/2005 | Chatterji |
| RE39,062 E | 4/2006 | Vinik et al. |
| RE39,299 E | 9/2006 | Vinik et al. |
| 7,166,439 B2 | 1/2007 | Vinik et al. |
| 7,393,919 B2 * | 7/2008 | Levetan et al. ................ 530/327 |
| 7,714,103 B2 * | 5/2010 | Levetan et al. ................ 530/326 |
| 7,989,415 B2 * | 8/2011 | Levetan et al. ................ 514/1.1 |
| 8,211,430 B2 * | 7/2012 | Levetan et al. ............. 424/133.1 |
| 2003/0035803 A1 | 2/2003 | McMichael |
| 2003/0212000 A1 | 11/2003 | Van Antwerp |
| 2004/0132644 A1 | 7/2004 | Vinik et al. |
| 2005/0084449 A1 | 4/2005 | Landes et al. |
| 2005/0249806 A1 | 11/2005 | Proehl et al. |
| 2006/0198839 A1 | 9/2006 | Levetan |
| 2007/0087971 A1 | 4/2007 | Levetan et al. |
| 2007/0184504 A1 | 8/2007 | Vinik et al. |
| 2008/0300190 A1 | 12/2008 | Levetan et al. |
| 2009/0068145 A1 | 3/2009 | Levetan et al. |
| 2009/0142338 A1 | 6/2009 | Levetan |
| 2010/0093605 A1 | 4/2010 | Levetan et al. |

FOREIGN PATENT DOCUMENTS

| | | |
|---|---|---|
| EP | 0303233 A2 | 2/1989 |
| EP | 239400 B1 | 8/1994 |
| EP | 1329458 A2 | 2/2000 |
| EP | 592106 B1 | 11/2004 |
| EP | 519596 B1 | 2/2005 |
| WO | WO 90/02809 A1 | 3/1990 |
| WO | WO 91/09967 A1 | 7/1991 |
| WO | WO 91/10737 A1 | 7/1991 |
| WO | WO 91/10741 A1 | 7/1991 |
| WO | WO 91/16428 A1 | 10/1991 |
| WO | WO 92/01047 A1 | 1/1992 |

(Continued)

OTHER PUBLICATIONS

Levetan et al. "Discovery of a Human Peptide Sequence Signaling Islet Neogenesis" Dec. 2008, *Endocrine Practice* 14(9):1075-1083.

(Continued)

*Primary Examiner* — Maury Audet
(74) *Attorney, Agent, or Firm* — Pepper Hamilton LLP

(57) ABSTRACT

Human proIslet Peptides (HIP) and HIP analogs and derivatives thereof, derived from or homologous in sequence to the human REG3A protein, chromosome 2p12, are able to induce islet neogenesis from endogenous pancreatic progenitor cells. Human proIslet Peptides are used either alone or in combination with other pharmaceuticals in the treatment of type 1 and type 2 diabetes and other pathologies related to aberrant glucose, carbohydrate, and/or lipid metabolism, insulin resistance, overweight, obesity, polycystic ovarian syndrome, eating disorders and the metabolic syndrome.

20 Claims, 7 Drawing Sheets

FOREIGN PATENT DOCUMENTS

| | | |
|---|---|---|
| WO | WO 92/18619 A1 | 10/1992 |
| WO | WO 92/22324 A1 | 12/1992 |
| WO | WO 93/11236 A1 | 6/1993 |
| WO | WO 93/17105 A1 | 9/1993 |
| WO | WO 95/15982 A2 | 6/1995 |
| WO | WO 95/20401 A1 | 8/1995 |
| WO | WO 96/19236 A1 | 6/1996 |
| WO | WO 96/26215 A1 | 8/1996 |
| WO | WO 96/33735 A1 | 10/1996 |
| WO | WO 96/34096 A1 | 10/1996 |
| WO | WO 97/13844 A1 | 4/1997 |
| WO | WO 98/16654 A1 | 4/1998 |
| WO | WO 98/24893 A2 | 6/1998 |
| WO | WO 98/46645 A2 | 10/1998 |
| WO | WO 98/50433 A2 | 11/1998 |
| WO | WO 03/033808 A2 | 4/2003 |
| WO | WO 03/094958 A1 | 11/2003 |
| WO | WO 03/105897 A1 | 12/2003 |
| WO | WO 2005/035761 A1 | 4/2005 |
| WO | WO 2006/096565 A2 | 9/2006 |
| WO | WO 2006/128083 A2 | 11/2006 |

OTHER PUBLICATIONS

Yang et al. "Lisofylline: a Potential Lead for the Treatment of Diabetes" Jan. 1, 2005, Biochemical Pharmacology 69(1):1-5.

Biron et al., A Monomeric 310-Helix is Formed in Water by a 13-Residue Peptide Representing the Neutralizing Determinant of HIV-1 on gp41, Biochemistry (2002) 41(42):12687-12696.

International Search Report and Written Opinion dated Dec. 23, 2008 (PCT/US2008/074868).

Mishra, et al., Studies of Synthetic Peptides of Human Apolipoprotein A-I Containing Tandem Amphipathic α-Helixes, Biochemistry (1998) 37(28):10313-10324.

Agardh, et al., Clinical evidence for the safety of GAD65 immunomodulation in adult-onset autoimmune diabetes, J. Diabetes Complications (2005) 19(4):238-246.

Ames, et al., Conversion of murine Fabs isolated from a combinatorial phage display library to full length immunoglobulins, J. Immunol. Methods (1995) 184:177-186.

Andersen, et al., Oral Glucose Augmentation of Insulin Secretion, J. Clin. Invest. (1978) 62:152-161.

Atherton, et al., Solid Phase Peptide Synthesis: A Practical Approach, IRL Press, Oxford (1989) (TOC).

Ausubel, et al., Current Protocols in Molecular Biology, vol. 1, John Wiley & Sons (2008) (TOC).

Ausubel, et al., Short Protocols in Molecular Biology, Current Protocols in Molecular Biology, $2^{nd}$ ed., John Wiley & Sons (1992) (TOC).

Baca, et al., Antibody Humanization Using Monovalent Phage Display, J. Biol. Chem. (1997) 272(16):10678-10684.

Bach, et al., Tolerance to Islet Autoantigens in Type 1 Diabetes, Ann. Rev. Immun. (2001) 19:131-161.

Better, et al., Escherichia coli Secretion of an Active Chimeric Antibody Fragment, Science (1988) 240:1041-1043.

Bitter, et al., Expression and Secretion Vectors for Yeast, Methods in Enzymol. (1987) 153:516-544.

Bodanszky Peptide Chemistry, A Practical Textbook, $2^{nd}$ ed., Springer-Verlag, Berlin (1993) (TOC).

Bonner-Weir, et al., The pancreatic ductal epithelium serves as a potential pool of progenitor cells, Pediatric Diabetes (2004) 5 (Suppl 2):16-22.

Brinkmann, et al., Phage display of disulfide-stabilized Fv fragments, J. Immunol. Methods (1995) 182:41-50.

Burton, et al., Human Antibodies from Combinatorial Libraries, Advances in Immunology (1994) 57:191-280.

Buse, et al., Amylin replacement with pramlinlide in type 1 and type 2 diabetes: A physiological approach to overcome barriers with insulin therapy, Clin. Diab. (2002) 20:137-144.

Caldas, et al., Design and synthesis of germline-based hemi-humanized single-chain Fv against the CD18 surface antigen, Protein Eng. (2000) 13(5):353-360.

Casteels, et al., Prevention of Type I Diabetes in Nonobese Diabetic Mice by Late Intervention with Nonhypercalcemic Analogs of 1,25-Dihydroxyvitamin $D_3$ in Combination with a Short Induction Course of Cyclosporin A, Endocrionology (1998) 139(1):95-102.

Cockett, et al., High Level Expression of Tissue Inhibitor of Metalloproteinases in Chinese Hamster Ovary Cells Using Glutamine Synthetase Gene Amplification, Bio/Technology (1990) 8:662-667.

Colbere-Garapin, et al., A New Dominant Hybrid Selective Marker for Higher Eukaryotic Cells, J. Mol. Biol. (1981) 150:1-14.

Couto, et al., Anti-BA46 Monoclonal Antibody Mc3: Humanization Using a Novel Positional Consensus and in Vivo and in Vitro Characterization, Cancer Res. (1995,) 55(8):1717-1722.

Couto, et al., Designing Human Consensus Antibodies with Minimal Positional Templates, Cancer Res. (1995) 55(23 Suppl):5973s-5977s.

Creutzfeldt, et al., Inhibition of Gastric Inhibitory Polypeptide (GIP) Release by Insulin and Glucose in Juvenile Diabetes, Diabetes (1980) 29(2):140-145.

Creutzfeldt, et al., New developments in the incretin concept, Diabetologia (1985) 28:565-573.

Creutzfeldt, The Incretin Concept Today, Diabetologia (1979) 16:75-85.

Davis, et al., The effects of HDV-insulin on carbohydrate metabolism in Type 1 diabetic patients, J. Diabetes Comp. (2001) 15(5):227-233.

Delovitch, et al., The Nonobese Diabetic Mouse as a Model of Autoimmune Diabetes: Immune Dysregulation Gets the NOD, Immunity (1997) 7:727-738.

Dicesar, et al., Vitamin D Deficiency is More Common in Type 2 Than in Type 1 Diabetes, Diabetes Care (Jan. 2006) 29(1):174.

Dupre, et al., Exendin-4 Normalized Postcibal Glycemic Excursions in Type 1 Diabetes, J. Clin. Endocrin. Metab. (2004) 89(7):3469-3473.

Dupre, et al., Stimulation of Insulin Secretion by Gastric Inhibitory Polypeptide in Man, J. Clin. Endocrin. Metab. (1973) 37:826-828.

Ebert, et al., Gastric Inhibitory Polypeptide, Clin. in Gastroenterology (1980) 9(3):679-698.

Edwards, et al., Glucagon-Like Peptide 1 Has a Physiological Role in the Control of Postprandial Glucose in Humans, Diabetes (1999) 48:86-93.

Elahi, et al., Pancreatic α- and β-cell responses to GIP infusion in normal man, Am. J. Physiol. (1979) 237:E185-E191.

Elahi, et al., The insulinotropic actions of glucose-dependent insulinotropic polypeptide (IP) and glucagon-like peptide-1 (7-37) in normal and diabetic subjects, Regulatory Peptide (1994) 51(1):63-74.

Foecking, et al., Powerful and versatile enhancer-promoter unit for mammalian expression vectors, Gene (1986) 45:101-105.

Gillies, et al., High-level expression of chimeric antibodies using adapted cDNA variable region cassettes, J. Immunol. Methods (1989) 125:191-202.

Grant, Epidemiology of disease risks in relation to vitamin D insufficiency, Prog. Biophys. Mol. Biol. (Feb. 28, 2006) 92:65-79.

Gutniak, et al., Subcutaneous Injection of the Incretin Hormone Glucagon-Like Peptide 1 Abolishes Postprandial Glycemia in NIDDM, Diabetes Care (1994) 17(9):1039-1044.

Haines, et al., Ex Vivo and In Vivo Gene Delivery to the Brain, Current Protocols in Human Genetics, John Wiley & Sons, NY (1994) 4(13).

Haines, et al., Vectors for Gene Therapy, Current Protocols in Human Genetics, John Wiley & Sons, NY (1994) 3(12).

Hammerling, et al., Monoclonal Antibodies and T-Cell Hybridomas, Perspectives and technical advances, Elsevier, NY (1981) (TOC).

Hao, et al., Beta-cell differentiation from nonendocrine epithelial cells of the adult human pancreas, Nature Medicine (2006) 12(3):310-316.

Harlow, et al., Antibodies: A Laboratory Manual, Cold Spring Harbor Laboratory Press, $2^{nd}$ ed. (1988) (TOC).

Heaney, et al., Human serum 25-hydroxycholecalciferol response to extended oral dosing with cholecalciferol[1-3], Am. J. Clin. Nutr. (2003) 77:204-210.

Herold, et al., A Single Course of Anti-CD3 Monoclonal Antibody hOKT3γ1 (Ala-Ala) Results in Improvement in C-Peptide Responses and Clinical Parameters for at Least 2 Years after Onset of Type 1 Diabetes, Diabetes (2005) 54(6):1763-1769.
Herold, et al., Anti-CD3 Monoclonal Antibody in New-Onset Type 1 Diabetes Melitus, New Eng. J. Med. (May 20, 2002) 346(22):1692-1698.
Holick, et al., Prevalence of Vitamin D Inadequacy among Postmenopausal North American Women Receiving Osteoporosis Therapy, J. Clin. Endocrinol. Metab. (2005) 90(6):3215-3224.
Holick, High Prevalence of Vitamin D Inadequacy and Implications for Health, Mayo Clin. Proc. (Mar. 2006) 81(3):353-373.
Holst, et al., Incretin hormones—an update, Scand. J. Clin. Lab. Invest. (2001) 61(Sup. 234):75-86.
Hopp, et al., Prediction of protein antigenic determinants from amino acid sequences, PNAS USA (1981) 78(6):3824-3828.
Ilic, et al., Is the paradoxical first trimester drop in insulin requirement due to an increase in C-peptide concentration in pregnant Type I diabetic women?, Diabetologia (2000) 43:1329-1330.
Inouye, et al., Up-promoter mutations in the Ipp gene of *Escherichia coli*, Nucleic Acids Res. (1985) 13(9):3101-3109.
International Search Report and Written Opinion dated Feb. 26, 2007 (PCT/US2006/020644).
International Search Report and Written Opinion dated Aug. 22, 2008 (PCT/US2007/85378).
Jamal, et al., Morphogenetic Plasticity of Adult Human Pancreatic Islets of Langerhans, Cell Death Differ. (Apr. 8, 2005) 12:702-712.
Jones, et al., A supplementary infusion of glucose-dependent insulinotropic polypeptide (GIP) with a meal does not significantly improve the β cell response or glucose tolerance in type 2 diabetes mellitus, Diabetes Res. Clin. Prect. (Nov. 6, 1989) 7(4):263-269.
Jovanovic, et al., Declining Insulin Requirement in the Late First Trimester of Diabetic Pregnancy, Diabetes Care (2001) 24:1130-1136.
Kettleborough, et al., Isolation of tumor cell-specific single-chain Fv from immunized mice using phage-antibody libraries and the reconstruction of whole antibodies from these antibody fragments, Eur. J. Immunol. (1994) 24:952-958.
Krarup, et al., Diminished Immumoreactive Gastric Inhibitory Polypeptide Response to a Meal in Newly Diagnosed Type 1 (Insulin-Dependent) Diabetics, J. Clin. Endocrin. Metab. (Jun. 1983) 56(6):1306-1312.
Krarup, et al., Effect of Porcine Gastric Inhibitory Polypeptide on β-cell Function in Type I and Type II Diabetes Mellitus, Metabolism (1987) 36(7):677-682.
Krarup, et al., Gastric Inhibitory Polypeptide in Newly Diagnosed Ketotic Type 1 (Insulin-dependent) Diabetics, Acta Med. Scand. (1988) 223(5):437-441.
Kreymann, et al., Glucagon-Like Peptide-1 7-36: A Physiological Incretin in Man, Lancet (1987) 2:1300-1304.
Kriegler, Gene Transfer and Expression, A Laboratory Manual, Stockton Press, NY (1990) (TOC).
Larsen, et al., Glucagon-Like Peptide-1 Infusion Must be Maintained for 24 h/day to Obtain Acceptable Glycemia in Type 2 Diabetic Patients Who Are Poorly Controlled on Sulphonylurea Treatment, Diabetes Care (2001) 24(8):1416-1421.
Larsen, et al., One-Week Continuous Infusion of GLP-1(7-37) Improves the Glycaemic Control in NIDDM, Abstracts from 56th Ann. Meeting in San Francisco, CA, Diabetes (1996) 45(Suppl. 2):860:233A (Abstract).
Lernmark, et al., Autoimmunity of Diabetes, Endocrinology and Metabolism Clinics of North America (1991) 20(3):589-617.
Levetan, et al., Impact of Pramlintide on Glucose Fluctuations and Postprandial Glucose, Glucagon, and Triglyceride Excursions Among Patients with Type 1 Diabetes Intensively Treated with Insulin Pumps, Diabetes Care (2003) 26(1):1-8.
Levetan, et al., Impact of Pramlintide on the Amplitude of Glycemic Excursions, Abstracts from 61st Ann. Meeting in San Francisco, CA, Diabetes (2001) 50(Suppl. 2):2105-PO:A501 (Abstract).
Levetan, et al., Reduced Glucose Fluctuations Following 4 Weeks of Pramlintide Treatment in Patients with Type 1 Diabetes Intensively Treated with Insulin Pumps, Abstracts from 62nd Ann. Meeting in San Francisco, CA, Diabetes (Jun. 2002) 51(Suppl. 2):429-P:A106 (Abstract).
Levetan, et al., Reduced Postprandial Glucose, Glueagon and Triglyceride Excursions Following 4 Weeks of Pramlintide Treatment in Patients with Type 1 Diabetes Treated Intensively with Insulin Pumps, Abstracts from 62nd Ann. Meeting in San Francisco, CA, Diabetes (Jun. 2002) 51(Suppl. 2):474-P:A117 (Abstract).
Lewis, et al., Improved glucose control in nonhospitalized pregnant diabetic patients, Obstet. & Gynecol. (1976) 48(3):260-267.
Li, et al., Islet loss and alpha cell expansion in type 1 diabetes induced by multiple low-dose streptozotocin administration in mice, J. Endocrinol. (2000) 165:93-99.
List, et al., Glucagon-like peptide 1 agonists and the development and growth of pancreatic β-cells, Am. J. Physiol. Endocrin. Metab. (2004) 286(6): E875-E881.
Logan, et al., Adenovirus tripartite leader sequence enhances translation of mRNAs late after infection, PNAS USA (1984) 81:3655-3659.
Ludvigsson et al., GAD Treatment and Insulin Secretion in Recent-Onset Type 1 Diabetes, N Engl J Med (Oct. 30, 2008) 359(18):1909-1920 (formerly 1-12).
Lugari, et al., Effect of Nutrient Ingestion on Glucagon-Like Peptide 1 (7-36 Amide) Secretion in Human Type 1 and Type 2 Diabetes, Horm. Metab. Res. (2000) 32:424-428.
Lynn, et al., A novel pathway for regulation of glucose-dependent insulinotropic polypeptide (GIP) receptor expression in β cells, FASEB (2003) 17:91-93.
Marquez, et al., Inositolphosphoglycans Possibly Mediate the Effects of Glucagon-Like Peptide-1 (7-36) amide on Rat Liver and Adipose Tissue, Cell Biochem. Funct. (1998) 16(1):51-56.
Mathis, et al., β-Cell death during progression to diabetes, Nature (Dec. 2001) 414(6865):792-798.
Meier, et al., Gastric Inhibitory Polypeptide: the neglected incretin revisited, Regulatory Peptides (2002) 107:1-13.
Meier, et al., Intravenous glucagon-like peptide 1 normalizes blood glucose after major surgery inpatients with type 2 diabetes, Critical Care Medicine (Mar. 2004) 32(3):848-851.
Meneilly, et al., Effects of 3 Months of Continuous Subcutaneous Administration of Glucagon-Like Peptide 1 in Elderly Patients with Type 2 Diabetes, Diabetes Care (2003) 26(10):2835-2841.
Merrifield, Solid Phase Peptide Synthesis, The Synthesis of a Tetrapeptide, J. Am. Chem. Soc. (1963) 85:2149-2154.
Morea, et al., Antibody Modeling: Implications for Engineering and Design, Methods (2000) 20(3):267-279.
Morgan, et al., Human Gene Therapy, Ann. Rev. Biochem. (1993) 62:191-217.
Morrison, Transfectomas Provide Novel Chimeric Antibodies, Science (1985) 229:1202-1207.
Mulligan, et al., Selection for animal cells that express the *Escherichin coli* gene coding for xanthine-guanine phosphoribosyltransferase, PNAS USA (1981) 78(4):2072-2076.
Mulligan, The Basic Science of Gene Therapy, Science (1993) 260:926-932.
Mullinax, et al., Expression of a Heterodimeric Fab Antibody Protein in One Cloning Step, BioTechniques (1992) 12(6):864-869.
Nauck, et al., Additive Insulinotropic Effects of Exogenous Synthetic Human Gastric Inhibitory Polypeptide and Glucagon-Like Peptide-1-(7-36) Amide Infused at Near-Physiological Insulinotropic Hormone and Glucose Concentrations, J. Clin. Endocrin. Metab. (1993) 76(4):912-917.
Nauck, et al., Effects of subcutaneous glucagon-like peptide 1 (GLP-1 [7-36 amide]) in patients with NIDDM, Diabetologia (1996) 39(12):1546-1553.
Ogawa, et al., Cure of Overt Diabetes in NOD Mice by Transient Treatment with Anti-Lymphocyte Serum and Exendin-4, Diabetes (2004) 53(7):1700-1705.
Ohare, et al., Transformation of mouse fibroblasts to methotrexate resistance by a recombinant plasmid expressing a prokaryotic dihydrofolate reductase, PNAS USA (1981) 78(3):1527-1531.
Oi, et al., Chimeric Antibodies, BioTechniques (1986) 4(3):214-222.
Padlan, A Possible Procedure for Reducing the Immunogenicity of Antibody Variable Domains While Preserving Their Ligand-Binding Properties, Molecular Immunology (1991) 28(4/5):489-498.

Pederson, et al., Comparison of Surface Accessible Residues in Human and Murine Immunoglobulin Fv Domains, J. Mol. Biol. (1994) 235(3):959-973.

Persic, et al., An integrated vector system for the eukaryotic expression of antibodies or their fragments after selection from phage display libraries, Gene (1997) 187:9-18.

Pozzilli, et al., Low Levels of 25-hydroxyvitamin $D_3$ and 1,25-dihydroxyvitamin $D_3$ in Patients with Newly Diagnosed Type 1 Diabetes, Horm. Metab. Res. (2005) 37(11):680-683.

Rabinovitch, et al., Combination Therapy With Sirolimus and Interleukin-2 Prevents Spontaneous and Recurrent Autoimmune Diabetes in NOD Mice, Diabetes (2002) 51:638-645.

Rafaeloff, et al., Cloning and Sequencing of the Pancreatic Islet Neogenesis Associated Protein (INGAP) Gene and Its Expression in Islet Neogenesis in Hamsters, J. Clin. Invest. (May 1997) 99(9):2100-2109.

Raz, et al., β-cell function in new-onset type 1 diabetes and immunomodulation with a heat-shock protein peptide (DiaPep277): a randomized, double-blind, phase II trial, Lancet (Nov. 2001) 358(9295):1749-1753.

Reis, et al., Vitamin D endocrine system and the genetic susceptibility to diabetes, obesity and vascular disease, A review of evidence, Diabetes Metab. (2005) 31:318-325.

Riachy, et al., 1,25-dihydroxyvitamin D3 protects human pancreatic islets against cytokine-induced apoptosis via down-regulation of the fas receptor, Apoptosis (Feb. 2006) 11(2):151-159.

Riechmann, et al., Reshaping human antibodies for therapy, Nature (1988) 332:323:327.

Rigg, et al., Effects of Exogenous insulin on excursions and diurnal rhythm of plasma glucose in pregnant diabetic patients with and without residual, Am. J. Obstet. Gynecol. (1980) 136:537-544.

Roguska, et al., A Comparison of two murine monoclonal antibodies humanized by CDR-grafting and variable domain resurfacing, Protein Eng. (Oct. 1996) (10):895-904.

Roguska, et al., Humanization of murine monoclonal antibodies through variable domain resurfacing, PNAS (1994) 91:969-973.

Ronit et al., Closing and Sequencing of the Pancreatic Islet Neogenesis Associated Protein (INGAP) Gene and Its Expression in Islet Neogenesis in Hamsters, J. CLin. Invest. (May 1997) 99(9):2100-2109.

Rosenberg, et al., A Pentadecapeptide Fragment of Islet Neogenesis-Associated Protein Increases Beta-Cell Mass and Reverses Diabetes in C57BL/6J Mice, Ann. Surg. (Nov. 2004) 240(5):875-884.

Rosenberg, et al., Induction of Islet Cell Differentiation and New Islet Formation in the Hamster-Further Support for a Ductular Origin, Pancreas (Jul. 1996) 13(1):38-46.

Rosenberg, et al., Islet-cell regeneration in the diabetic hamster pancreas with restoration of normoglycaemia can be induced by a local growth factor(s), Diabetologia (Mar. 1996) 39(3):256-262.

Rosenberg, et al., Trophic Stimulation of the Ductular-Islet Cell Axis: A New Approach to the Treatment of Diabetes, Adv. Exp. Med. Biol. (1992) 321:95-104.

Sandhu, A rapid procedure for the humanization of monoclonal antibodies, Gene (1994) 150(2):409-410.

Santerre, et al., Expression of prokaryotic genes for hygromycin B and G418 resistance as dominant-selection markers in mouse L cells, Gene (1984) 30:147-156.

Sawai, et al., Direct Production of the Fab Fragment Derived from the Sperm Immobilizing Antibody Using Polymerase Chain Reaction and cDNA Expression Vectors, AJRI (1995) 34:26-34.

Scopes, Protein Purification, Principles and Practice, $3^{rd}$ ed., Springer, NY (1994) (TOC).

Studnicka, et al., Human-engineered monoclonal antibodies retain full specific binding activity by preserving non-CDR complementarity-modulating residues, Protein Engineering (1994) 7(6):805-814.

Tam, et al., INGAP Peptide improves nerve function and enhances regeneration in streptozotocin-induced diabetic C57BL/6 mice, FASEB J. (Sep. 2, 2004) 18(4):1-23.

Tan, et al., 'Superhumanized' Antibodies: Reduction of Immunogenic Potential by Complementarity-Determining Region Grafting with Human Germline Sequences: Application to an Anti-CD28, J. Immunol. (2002) 169:1119-1125.

Thorens, et al., Glucagon-Like Peptide-1 and Control of Insulin Secretion, Diabetes Metab. (1995) 21(5):311-318.

Tolstoshev, Gene Therapy, Concepts, Current Trials and Future Directions, Ann. Rev. Pharmacol. Toxicol. (1993) 32:573-596.

Van Heeke, et al., Expression of Human Asparagine Synthetase in *Escherichia coli*, J. Biol. Chem. (1989) 264(10):5503-5509.

Vieth, et al., Efficacy and safety of vitamin D3 intake exceeding the lowest observed adverse effect level 1-3, Am. J. Clin. Nutr. (2001) 73:288-294.

Vilsboll, et al., Incretin Secretion in Relation to Meal Size and Body Weight in Healthy Subjects and People with Type 1 and Type 2 Diabetes Mellitus, J. Clin. Endocrin. Metab. (2003) 88(6):2706-2713.

Vinik, et al., Induction of Pancreatic Islet Neogenesis, Horm. Metab. Res. (Jun. 1997) 29(7):278-293.

Vukkadapu, et al., Dynamic interaction between T cell-mediated β-cell damage and β-cell repair in the run up to autoimmune diabetes of the NOD mouse, Physiol. Genomics (2005) 21(2):201-211.

Wang, et al., Glucagon-like peptide-1 Can Reverse the Age-related Decline in Glucose Tolerance in Rats, J. Clin. Invest. (Jun. 1997) 99(12):2883-2889.

Want, et al., Reduced Postprandial Glucose, Glucagon and Triglyceride Excursions Following 4 Weeks of Pramlintide Treatment in Patients with Type 1 Diabetes Treated Intensively with Insulin Pumps, Diabetes (Jun. 14, 2002) 51(suppl. 2):474-P.

Wigler, et al., Transformation of mammalian cells with an amplifiable dominant-acting gene, Proc. Natl. Acad. Sci. USA (Jun. 1980) 77(6):3567-3570.

Wu, et al., Adapters, Linkers and Methylation, Methods in Enzymol. (1987) 152:343-349.

Wu, et al., Delivery systems for gene therapy, Biotherapy (1991) 3(1):87-95.

Xu, et al., Exendin-4 Stimulates Both β-Cell Replication and Neogenesis, Resulting in Increased β-Cell Mass and Improved Glucose Tolerance in Diabetic Rats, Diabetes (Dec. 1999) 48:2270-2276.

Yamaoka, Regeneration therapy for diabetes mellitus, Expert Opin. Biol. Ther. (2003) 3(3):425-433.

Yoon, et al., Selective β-Cell Loss and α-Cell Expansion in Patients with Type 2 Diabetes Mellitus in Korea, J. Clin. Endocrinol. Metab. (May 2003) 88(5):2300-2308.

Young, et al., Amylin's physiology and its role in diabetes, Curr. Opin. Endocrin. Diabetes (1997) 4(4):282-290.

Zander, et al., Effect of 6-week course of glucagon-like peptide 1 on glycaemic control, insulin sensitivity, and β-cell function in type 2 diabetes: a parallel-group study, Lancet (Mar. 2002) 359:824-830.

Igarashi, et al. Role of GLP-1, *Internal Secretion/Diabetes Department*, Jan. 28, 2005, vol. 20, No. 1, p. 69-74.

Dusetti et al. "Molecular Cloning, Genomic Organization, and Chromosomal Localization of the Human Pancreatitis-Associated Protein (PAP) Gene" 1994, Genomics 19:108-114.

Bach, et al., Tolerance to Islet Autoantigens in Type 1 Diabetes, Ann. Rev. Immun. (Apr. 2001) 19:131-161.

Haines, et al., Ex Vivo and In Vivo Gene Delivery to the Brain, Current Protocols in Human Genetics, John Wiley & Sons, NY (Apr. 1994) vol. 4, Chap. 13: 1-36.

Haines, et al., Vectors for Gene Therapy, Current Protocols in Human Genetics, John Wiley & Sons, NY (Apr. 1994) vol. 3, Chap. 12: 1-264.

Heaney, et al., Human serum 25-hydroxycholecalciferol response to extended oral dosing with cholecalciferol1-3, Am. J. Clin. Nutr. (Jan. 2003) 77(1):204-210.

International Search Report and Written Opinion dated Dec. 23, 2008.

International Search Report and Written Opinion dated Feb. 26, 2007.

International Search Report and Written Opinion dated Aug. 22, 2008.

Lernmark, et al., Autoimmunity of Diabetes, Endocrinology and Metabolism Clinics of North America (Sep. 1991) 20(3):589-617.

Levetan, et al., Impact of Pramlintide on Glucose Fluctuations and Postprandial Glucose, Glucagon, and Triglyceride Excursions Among Patients with Type 1 Diabetes Intensively Treated with Insulin Pumps, Diabetes Care (Jan. 2003) 26(1):1-8.

Levetan, et al., Impact of Pramlintide on the Amplitude of Glycemic Excursions, Abstracts from 61st Ann. Meeting in San Francisco, CA, Diabetes (Jun. 22-26, 2001) 50(Suppl. 2):2105-PO:A501 (Abstract).

Levetan, et al., Reduced Glucose Fluctuations Following 4 Weeks of Pramlintide Treatment in Patients with Type 1 Diabetes Intensively Treated with Insulin Pumps, Abstracts from 62nd Ann. Meeting in San Francisco, CA, Diabetes (Jun. 14-18, 2002) 51(Suppl. 2):429-P:A106 (Abstract).

* cited by examiner

A

B

A

B

```
                          SEQUENCE LISTING

<160> NUMBER OF SEQ ID NOS: 28

<210> SEQ ID NO 1
<211> LENGTH: 175
<212> TYPE: PRT
<213> ORGANISM: Homo sapiens

<400> SEQUENCE: 1

Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
                20                  25                  30

Leu Pro Ser Ala Arg Ile Arg Cys Pro Lys Gly Ser Lys Ala Tyr Gly
            35                  40                  45

Ser His Cys Tyr Ala Leu Phe Leu Ser Pro Lys Ser Trp Thr Asp Ala
        50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
                100                 105                 110

Thr Glu Pro Asn Gly Glu Gly Trp Glu Trp Ser Ser Ser Asp Val Met
            115                 120                 125

Asn Tyr Phe Ala Trp Glu Arg Asn Pro Ser Thr Ile Ser Ser Pro Gly
        130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175

<210> SEQ ID NO 2
<211> LENGTH: 15
<212> TYPE: PRT
<213> ORGANISM: Homo sapiens

<400> SEQUENCE: 2

Ile Gly Leu His Asp Pro Thr Gln Gly Thr Glu Pro Asn Gly Glu
1               5                   10                  15

<210> SEQ ID NO 3
<211> LENGTH: 14
<212> TYPE: PRT
<213> ORGANISM: Homo sapiens

<400> SEQUENCE: 3
```

```
Ile Gly Leu His Asp Pro Thr Gln Gly Thr Glu Pro Asn Gly
1               5                  10
```

<210> SEQ ID NO 4
<211> LENGTH: 17
<212> TYPE: PRT
<213> ORGANISM: Homo sapiens

<400> SEQUENCE: 4

```
Val Trp Ile Gly Leu His Asp Pro Thr Gln Gly Thr Glu Pro Asn Gly
1               5                   10                  15

Glu
```

<210> SEQ ID NO 5
<211> LENGTH: 6
<212> TYPE: PRT
<213> ORGANISM: Homo sapiens

<400> SEQUENCE: 5

```
Ile Gly Leu His Asp Pro
1               5
```

<210> SEQ ID NO 6
<211> LENGTH: 7
<212> TYPE: PRT
<213> ORGANISM: Homo sapiens

<400> SEQUENCE: 6

```
Trp Ile Gly Leu His Asp Pro
1               5
```

<210> SEQ ID NO 7
<211> LENGTH: 15
<212> TYPE: PRT
<213> ORGANISM: Homo sapiens

<400> SEQUENCE: 7

```
Trp Ile Gly Leu His Asp Pro Thr Gln Gly Thr Glu Pro Asn Gly
1               5                   10                  15
```

<210> SEQ ID NO 8
<211> LENGTH: 173
<212> TYPE: PRT
<213> ORGANISM: Mesocricetus auratus

<400> SEQUENCE: 8

```
Met Met Leu Pro Met Thr Leu Cys Arg Met Ser Trp Met Leu Leu Ser
1               5                   10                  15

Cys Leu Met Phe Leu Ser Trp Val Glu Gly Glu Ser Gln Lys Lys
            20                  25                  30

Leu Pro Ser Ser Arg Ile Thr Cys Pro Gln Gly Ser Val Ala Tyr Gly
            35                  40                  45

Ser Tyr Cys Tyr Ser Leu Ile Leu Ile Pro Gln Thr Trp Ser Asn Ala
        50                  55                  60

Glu Leu Ser Cys Gln Met His Phe Ser Gly His Leu Ala Phe Leu Leu
65                  70                  75                  80

Ser Thr Gly Glu Ile Thr Phe Val Ser Ser Leu Val Lys Asn Ser Leu
                85                  90                  95

Thr Ala Tyr Gln Tyr Ile Trp Ile Gly Leu His Asp Pro Ser His Gly
                100                 105                 110

Thr Leu Pro Asn Gly Ser Gly Trp Lys Trp Ser Ser Ser Asn Val Leu
```

```
                115                 120                 125
Thr Phe Tyr Asn Trp Glu Arg Asn Pro Ser Ile Ala Ala Asp Arg Gly
        130                 135                 140

Tyr Cys Ala Val Leu Ser Gln Lys Ser Gly Phe Gln Lys Trp Arg Asp
145                 150                 155                 160

Phe Asn Cys Glu Asn Glu Leu Pro Tyr Ile Cys Lys Phe
                165                 170
```

<210> SEQ ID NO 9
<211> LENGTH: 6
<212> TYPE: PRT
<213> ORGANISM: Homo sapiens

<400> SEQUENCE: 9

```
Gly Leu His Asp Pro Thr
1               5
```

<210> SEQ ID NO 10
<211> LENGTH: 6
<212> TYPE: PRT
<213> ORGANISM: Homo sapiens

<400> SEQUENCE: 10

```
Leu His Asp Pro Thr Gln
1               5
```

<210> SEQ ID NO 11
<211> LENGTH: 6
<212> TYPE: PRT
<213> ORGANISM: Homo sapiens

<400> SEQUENCE: 11

```
His Asp Pro Thr Gln Gly
1               5
```

<210> SEQ ID NO 12
<211> LENGTH: 6
<212> TYPE: PRT
<213> ORGANISM: Homo sapiens

<400> SEQUENCE: 12

```
Asp Pro Thr Gln Gly Thr
1               5
```

<210> SEQ ID NO 13
<211> LENGTH: 6
<212> TYPE: PRT
<213> ORGANISM: Homo sapiens

<400> SEQUENCE: 13

```
Pro Thr Gln Gly Thr Glu
1               5
```

<210> SEQ ID NO 14
<211> LENGTH: 6
<212> TYPE: PRT
<213> ORGANISM: Homo sapiens

<400> SEQUENCE: 14

```
Thr Gln Gly Thr Glu Pro
1               5
```

<210> SEQ ID NO 15
<211> LENGTH: 6

```
<212> TYPE: PRT
<213> ORGANISM: Homo sapiens

<400> SEQUENCE: 15

Gln Gly Thr Glu Pro Asn
1               5

<210> SEQ ID NO 16
<211> LENGTH: 6
<212> TYPE: PRT
<213> ORGANISM: Homo sapiens

<400> SEQUENCE: 16

Gly Thr Glu Pro Asn Gly
1               5

<210> SEQ ID NO 17
<211> LENGTH: 6
<212> TYPE: PRT
<213> ORGANISM: Homo sapiens

<400> SEQUENCE: 17

Thr Glu Pro Asn Gly Glu
1               5

<210> SEQ ID NO 18
<211> LENGTH: 7
<212> TYPE: PRT
<213> ORGANISM: Homo sapiens

<400> SEQUENCE: 18

Ile Gly Leu His Asp Pro Thr
1               5

<210> SEQ ID NO 19
<211> LENGTH: 16
<212> TYPE: PRT
<213> ORGANISM: Homo sapiens

<400> SEQUENCE: 19

Trp Ile Gly Leu His Asp Pro Thr Gln Gly Thr Glu Pro Asn Gly Glu
1               5                   10                  15

<210> SEQ ID NO 20
<211> LENGTH: 16
<212> TYPE: PRT
<213> ORGANISM: Pan troglodytes

<400> SEQUENCE: 20

Trp Ile Gly Leu His Asp Pro Thr Gln Gly Ser Glu Pro Asp Gly Gly
1               5                   10                  15

<210> SEQ ID NO 21
<211> LENGTH: 16
<212> TYPE: PRT
<213> ORGANISM: Mesocricetus auratus

<400> SEQUENCE: 21

Trp Ile Gly Leu His Asp Pro Ser His Gly Thr Leu Pro Asn Gly Ser
1               5                   10                  15

<210> SEQ ID NO 22
<211> LENGTH: 16
<212> TYPE: PRT
<213> ORGANISM: Mus musculus
```

-continued

```
<400> SEQUENCE: 22

Trp Ile Gly Leu His Asp Pro Thr Met Gly Gln Gln Pro Asn Gly Gly
1               5                   10                  15

<210> SEQ ID NO 23
<211> LENGTH: 16
<212> TYPE: PRT
<213> ORGANISM: Rattus norvegicus

<400> SEQUENCE: 23

Trp Ile Trp Leu His Asp Pro Thr Met Gly Gln Gln Pro Asn Gly Gly
1               5                   10                  15

<210> SEQ ID NO 24
<211> LENGTH: 16
<212> TYPE: PRT
<213> ORGANISM: Bos taurus

<400> SEQUENCE: 24

Trp Ile Gly Leu His Asp Pro Thr Glu Gly Ser Glu Pro Asp Ala Gly
1               5                   10                  15

<210> SEQ ID NO 25
<211> LENGTH: 16
<212> TYPE: PRT
<213> ORGANISM: Canis familiaris

<400> SEQUENCE: 25

Trp Met Gly Leu His Asp Pro Thr Glu Gly Tyr Glu Pro Asn Ala Asp
1               5                   10                  15

<210> SEQ ID NO 26
<211> LENGTH: 16
<212> TYPE: PRT
<213> ORGANISM: Ovis aries

<400> SEQUENCE: 26

Trp Ile Gly Leu His Asp Pro Thr Glu Gly Ser Glu Pro Asn Ala Gly
1               5                   10                  15

<210> SEQ ID NO 27
<211> LENGTH: 15
<212> TYPE: PRT
<213> ORGANISM: Hamster sp.

<400> SEQUENCE: 27

Ile Gly Leu His Asp Pro Ser His Gly Thr Leu Pro Asn Gly Ser
1               5                   10                  15

<210> SEQ ID NO 28
<211> LENGTH: 15
<212> TYPE: PRT
<213> ORGANISM: Artificial
<220> FEATURE:
<223> OTHER INFORMATION: Scrambled sequence

<400> SEQUENCE: 28

Asp Gly Gly Thr Pro Gln Pro Gly Asn Trp Ile Glu Leu Thr His
1               5                   10                  15
```

PEPTIDES, DERIVATIVES AND ANALOGS THEREOF, AND METHODS OF USING SAME

CROSS REFERENCE TO RELATED APPLICATIONS

This application is a continuation application of pending U.S. application Ser. No. 12/635,053, filed Dec. 10, 2009, which is a divisional application of U.S. application Ser. No. 12/121,123 filed on May 15, 2008, now U.S. Pat. No. 7,714,103, dated May 11, 2010, which is a continuation application of U.S. application Ser. No. 11/441,491 filed on May 25, 2006, now U.S. Pat. No. 7,393,919, dated Jul. 1, 2008, which claims the benefit of U.S. Provisional Application No. 60/684,819, filed on May 25, 2005; all aforementioned applications are herein incorporated by reference in their entirety.

REFERENCE TO GOVERNMENT GRANT

Not Applicable.

JOINT RESEARCH AGREEMENT

Not Applicable.

FIELD OF THE INVENTION

The present invention provides peptides and analogs thereof and methods of using them for treating type 1 diabetes mellitus, type 2 diabetes mellitus and other conditions. The invention relates to the fields of molecular biology, biology, chemistry, medicinal chemistry, and pharmacology.

BACKGROUND OF THE INVENTION

Since 1922, insulin has been the only available therapy for the treatment of type 1 diabetes and other conditions related to the lack of or diminished efficacy or production of insulin. However, diabetic patients on insulin do not have normal glucose metabolism, because insulin is only part of the missing and aberrant pancreatic function. Despite decades of research and the advent of pancreatic islet transplantation in 1974 and newer claims of success resulting from the Edmonton Protocol for islet transplantation, these approaches have not been very successful in the United States. For example, at four years post-transplant, fewer than 10% of patients who have received islet transplants remain insulin independent. Additionally, there is an 18% rate of serious side effects.

Investigators have also researched whether endogenous production of insulin can be stimulated by drug treatment. For example, over the past several decades, several therapies have been studied which are involved in glucose metabolism, and analogs of these peptides have been identified. These therapies include sequences which are similar to Glucagon Like Peptide-1 (GLP-1) and include: GLP-1 receptor analogs, Exendin-4, Exenatide/BYETTA™, which is derived from the Gila Monster, Gastric Inhibitory Peptide/Glucose-Dependent Insulinoptropic polypeptide (GIP), and compounds homologous to GLP-1, such as Liraglutide (NN2211), Dipeptidyl Peptidase-4 Inhibitors, which inhibit the breakdown of GLP-1, Gastrin, Epidermal Growth Factor and Epidermal Growth Factor Analogs, and Hamster derived Islet Neogenesis Associated Peptide (INGAP).

More specifically, hamster INGAP fragments have been identified (see Ronit, R, et al. *Journal of Clinical Investigation* May 1997, vol 99 (9): 2100-2109; U.S. Pat. No. 5,834,590; and U.S. Patent Application Publication No. 2004/0132644). Hamster-derived INGAP may be effective in facilitating pancreatic islet neogenesis. However, INGAP is not a human peptide, and thus may not be as efficacious and could produce an adverse immune response in some subjects.

Proof of the elasticity of the pancreas with respect to the generation of new pancreatic islets throughout one's lifetime accompanied by pancreatic islet death or apoptosis has replaced the long held concept that the number of insulin producing islet structures is fixed at birth and maintained throughout life, whereas the plasticity and ability of beta cells to proliferate within existing islets has been well established. It is currently accepted that pancreatic islet neogenesis occurs from preexisting pancreatic cells through differentiation of progenitor cells found amongst both the endocrine and exocrine fractions of the pancreas. Data demonstrates that, even decades after the onset of type 1 diabetes, insulin producing islets can be regenerated. For example, patients with type 1 diabetes who can make normal levels of C-peptide during pregnancy. Several teams have found a paradoxical rise in C-peptide levels during the first trimester of pregnancy into the normal range in as many as one-third of all pregnant type 1 patients (Lewis et al., 1976, Rigg et al., 1980, Ilic et al., 2000, Jovanovic et al., 2001). This rise in C-peptide is accompanied by a significant reduction in insulin requirements with some patients being able to completely discontinue insulin transiently during the first trimester of pregnancy. This rise in C-peptide during pregnancy that occurs within 10 weeks of gestation among patients, despite no measurable C-peptide prior to pregnancy, implies the restoration of functioning islet structures. It is hypothesized that the islet neogenesis that occurs during pregnancy results from the concomitant rise in endogenous steroid production and a down regulation of the immune system preventing immune attack on the fetus, which likely also plays a role in suppression of lymphocyte attack on the islets. Along with immune suppression, it is also speculated that there is an up regulation of maternal islet growth promoting factors during pregnancy to compensate for the lowering of the maternal glucose setpoint in pregnancy. Similarly, patients who have been on long term immunosuppression for kidney transplantation have been observed to regenerate insulin producing islets.

Over the past decade, clinical trials have been conducted to evaluate the impact of a number of immune modulators that may arrest the destruction of the beta cells of the pancreas. Anti CD-3 antibodies (hOKT3γ1(Ala-Ala and ChAglyCD3) that target the immune response and specifically block the T-lymphocytes that cause beta cell death in type 1 diabetes have been utilized, as have, Sirolimus (Rapamycin), Tacrolimus (FK506), a heat-shock protein 60 (DIAPEP277™) an anti-Glutamic Acid Decarboxylase 65 (GAD65) vaccine, Mycophenolate Mofetil alone or in combination with Daclizumab, the anti-CD20 agent, lysofylline, Rituximab, Campath-1H (Anti-CD52 Antibody) and Vitamin D, IBC-VSO vaccine which is a synthetic, metabolically inactive form of insulin designed to prevent pancreatic beta-cell destruction, interferon-α vaccination using $CD4^+CD25^+$ antigen-specific regulatory T cells or a similar agent is used in the combination therapy approaches to utilizing regulatory T cells either directly or through the use of immunotherapy to arrest the destruction of insulin-producing cells. The aim of these trials is to determine the ability of such agents to preserve islet function by preventing further immune attack on the beta cells of the islets of the pancreas.

Additionally, recent studies have found that vitamin D may play an important immune modulating role in the prevention of type 1 diabetes. Up to 54.7% of populations in the US, regardless of latitude, have low 25 hydroxyvitamin D levels (Holick, *J Clin Endorinol Metab* 2005; 90-3215-3224). Vitamin D deficiency has been demonstrated, not only to be associated with the increased risk of type 1 diabetes and seen at the onset of type 1 diagnosis, but also is commonly seen among both patients with type 1 and 2 diabetes. Maintaining levels above 40 ng/ml are recommended to sustain normal immune function (Riachy *Apoptosis*. 2006 February; 11(2): 151-9. Holick. *Mayo Clin Proc*. 2006 March; 81(3):353-73, Grant. *Prog Biophys Mol. Biol*. 2006 Feb. 28; [Epub ahead of print]. DiCesar. *Diabetes Care*. 2006 January; 29(1):174, Reis. *Diabetes Metab*. 2005; 31(4 Pt 1):318-25, Pozzilli. *Horm Metab Res*. 2005; 37(11):680-3). No adverse effects have been seen with dosages up to 10,000 IU/day (Heaney. *Am J Clin Nutr*, 204-210, Vieth. *Am J Clin Nutr*. 2001; 73:288-294).

To date, however, there has been no single or combination therapy that has been successfully used to treat the underlying disease mechanisms of type 1 diabetes, type 2 diabetes or conditions in which there is a lack of or diminished insulin production and/or alterations in glucose metabolism or insulin secretion, including obesity, overweight, insulin resistant syndromes and the metabolic syndrome. There remains a need for new treatments methods and pharmaceutical compositions, which address the underlying mechanisms for the alterations in type 1 diabetes mellitus, type 2 diabetes mellitus and conditions in which there is an alteration in insulin secretion. Especially needed are methods and compositions that can also treat the many other conditions in which the lack of, or diminished, insulin production has a causative role or contributes to the symptoms of patients in need of treatment. At present, there appears to be no treatment that ameliorates the symptoms of type 1 diabetes by targeting the mechanisms underlying all of these disease states. The present invention meets the need for improved therapies for treating type 1 diabetes, type 2 diabetes and other conditions.

SUMMARY OF THE INVENTION

The invention provides a Human proIslet Peptide (HIP) or an analog or a derivative thereof comprising the amino acid sequence of SEQ ID NO:13. In one embodiment of the HIP or an analog or a derivative thereof, the HIP or an analog or a derivative thereof is less than 17 amino acids in length. In one aspect of this embodiment of the invention, HIP or an analog or a derivative thereof comprises an amino acid sequence selected from a member of the group consisting of SEQ ID NOs:2, 3, 4, 5, 6, 7, 18 and 19. The invention also provides pharmaceutical preparations comprising the HIP or an analog or derivative together with a pharmaceutically acceptable excipient.

The invention also provides a method of treating a pathology associated with impaired pancreatic function in a subject in need of such treatment. The method is practiced by administering to the patient a therapeutic amount of one or more Human proIslet Peptides or analogs or derivatives thereof, thereby treating type 1 or type 2 diabetes in the subject. In one embodiment of the method of treating type 1 or type 2 diabetes, the Human proIslet Peptide comprises an amino acid sequence selected from a member of the group consisting of SEQ ID NOs:2, 3, 4, 5, 6, 7, 18 and 19. In one aspect of this embodiment, the Human proIslet Peptide is 17 amino acids in length or less.

In another embodiment of the method of treating a pathology associated with impaired pancreatic function in a subject in need of such treatment, the method further comprises the step of administering one or more agents for stimulating pancreatic islet cell regeneration. In one aspect of this embodiment, the agents are selected from a member of the group consisting of Human proIslet Peptide, amylin/Pramlintide (SYMLIN™), exendin-4 (EXENATIDE™), GIP, GLP-1, GLP-1 receptor agonists, GLP-1 analogs, hamster INGAP, Liraglutide (NN2211) or a dipeptidyl peptidase inhibitor, which blocks the degradation of GLP-1.

In another embodiment of the method of treating a pathology associated with impaired pancreatic function in a subject in need of such treatment, the method further comprises the steps of 1) intensifying glycemic control 2) the addition of oral vitamin D3 (cholecalciferol) to maintain 25-hydroxyvitamin levels above 40 ng/ml 3) the addition of one or more immune therapies for protecting new islet cell formation 4) administration of HIP or HIP analogs for stimulating pancreatic islet cell regeneration, while tapering off insulin 5) repeated therapy for protection of islets on a 3 to 24 month basis, dependent on the selected immune therapy and 6) Maintenance of 25-hydroxyvitamin D levels above 40 ng/ml with oral vitamin D3 (cholecalciferol).

In another embodiment of the method of treating a pathology associated with impaired pancreatic function in a subject in need of such treatment, the method further comprises the steps which may include: 1) intensifying glycemic control 2) the addition of vitamin (cholecalciferol) to maintain 25-hydroxyvitamin levels above 40 ng/ml 3) administration of an agent for stimulating pancreatic islet regeneration including the administration of HIP or HIP analogs 4) Co-administration of a member of the group consisting of amylin/Pramlintide (SYMLIN™), exendin-4 (EXENATIDE™), GIP, GLP-1, GLP-1 receptor agonists, GLP-1 analogs, INGAP, Liraglutide (NN2211) or a dipeptidyl peptidase inhibitor, which blocks the degradation of GLP-1, while tapering off diabetes therapy and 5) maintaining levels of 25-hydroxy vitamin D above 40 ng/ml with oral Vitamin D3 (cholecalciferol).

In one aspect of this embodiment, the agents for stimulating pancreatic islet or beta cell regeneration are selected from a member of the group consisting of HIP and HIP analogs, exendin-4 (EXENATIDE/BYETTA™), Gastrin, Epidermal Growth Factor and Epidermal Growth Factor analog, GIP, GLP-1, GLP-1 receptor agonists, GLP-1 analogs, INGAP, Liraglutide (NN2211) and/or Dipeptidyl Peptidase 4 Inhibitors.

In another embodiment of the method of treating a pathology associated with impaired pancreatic function in a subject in need of such treatment, the method further comprises the step of administering one or more agents that inhibit, block, or destroy the autoimmune cells that target pancreatic islets. In one aspect of this embodiment, the agents that inhibit, block, or destroy the autoimmune cells that target pancreatic islets are selected from the group consisting of Anti CD-3 antibodies (hOKT3γ1(Ala-Ala and ChAglyCD3) that target the immune response and specifically block the T-lymphocytes that cause beta cell death in type 1 diabetes, as well as, Sirolimus (Rapamycin), Tacrolimus (FK506), a heat-shock protein 60 (Diapep277) an anti-Glutamic Acid Decarboxylase 65 (GAD65) vaccine, Mycophenolate Mofetil alone or in combination with Daclizumab, the anti-CD20 agent, Rituximab, Campath-1H (Anti-CD52 Antibody), lysofylline, Vitamin D, IBC-VSO vaccine which is a synthetic, metabolically inactive form of insulin designed to prevent pancreatic beta-cell destruction, interferon-alpha, vaccination using $CD4^+$ $CD25^+$ antigen-specific regulatory T cells or a similar agent is used in the combination therapy approaches to utilizing regulatory T cells either directly or through the use of immunotherapy to arrest the destruction of insulin-producing cells.

In another embodiment of the method of treating a pathology associated with impaired pancreatic function in a subject in need of such treatment, at least one symptom of the pathology associated with impaired pancreatic function is treated or reduced as a result of the administration of at least one Human proIslet Peptide. In one aspect of this embodiment, the symptom is selected from a member of the group consisting of low levels of insulin or insulin activity, insulin resistance, hyperglycemia, hemoglobin A1C level greater than 6.0%, frequent urination, excessive thirst, extreme hunger, unusual weight loss or gain, being overweight, increased fatigue, irritability, blurry vision, genital itching, odd aches and pains, dry mouth, dry or itchy skin, impotence, vaginal yeast infections, poor healing of cuts and scrapes, excessive or unusual infections, loss or worsening of glycemic control, fluctuations in blood glucose, fluctuations in blood glucagon, and fluctuations in blood triglycerides, with hyperglycemia ultimately leading to microvascular and macrovascular complications, which include visual symptoms that lead to blindness, accelerated kidney impairment that can lead to renal failure necessitating dialysis or kidney transplant and neuropathy leading to foot ulcers and amputations. Additionally, recent studies have demonstrated both microvascular and macrovascular/cardiovascular risk reduction among type 1 diabetes patients who have improved glycemic control.

In another embodiment of the method of treating a pathology associated with impaired pancreatic function in a subject in need of such treatment, the pathology associated with impaired pancreatic function is any one of type 1 diabetes, new onset type 1 diabetes, type 2 diabetes, latent autoimmune diabetes of adulthood, pre-diabetes, impaired fasting glucose, impaired glucose tolerance, insulin resistant syndrome, metabolic syndrome, being overweight, obesity, hyperlipidemia, hypertriglyceridemia, eating disorders and polycystic ovarian syndrome.

The invention also provides an antibody which selectively binds to a HIP or analog or derivative thereof comprising an amino acid sequence selected from a member of the group consisting of SEQ ID NOs:2, 3, 4, 5, 6, 7, 18 and 19. In one embodiment, the antibody is a monoclonal antibody. In another embodiment, the antibody is a polyclonal antibody. Such antibodies can be used in diagnostic methods provided by the invention, which methods comprise detecting HIP or analog or derivative levels in the serum or tissue of a mammal. In one embodiment, such methods are used to diagnose a disease or condition related to aberrant HIP levels; in another embodiment, the diagnostic method is used to monitor treatment with HIP or an analog or derivative to ensure that therapeutically effective levels are being achieved in a patient receiving such therapy.

The invention also provides a kit for treating a patient having type 1 or type 2 diabetes or other condition in which there are aberrant insulin levels, perturbation in glucose metabolism or insulin resistance, comprising a therapeutically effective dose of a Human proIslet Peptide and optionally at least one agent for stimulating GLP-1 receptors or enhancing GLP-1 levels, promoting beta cell regeneration, increased satiety, decreased food intake and weight loss, while reducing needs for insulin and other diabetic agents either in the same or separate packaging, and instructions for its use. The invention also provides a kit for measuring HIP levels in a sample, the kit comprising a HIP-specific antibody and optionally HIP and optionally a labeling means.

These and other aspects and embodiments of the invention are described in greater detail below.

DETAILED DESCRIPTION OF THE INVENTION

Figure 1:
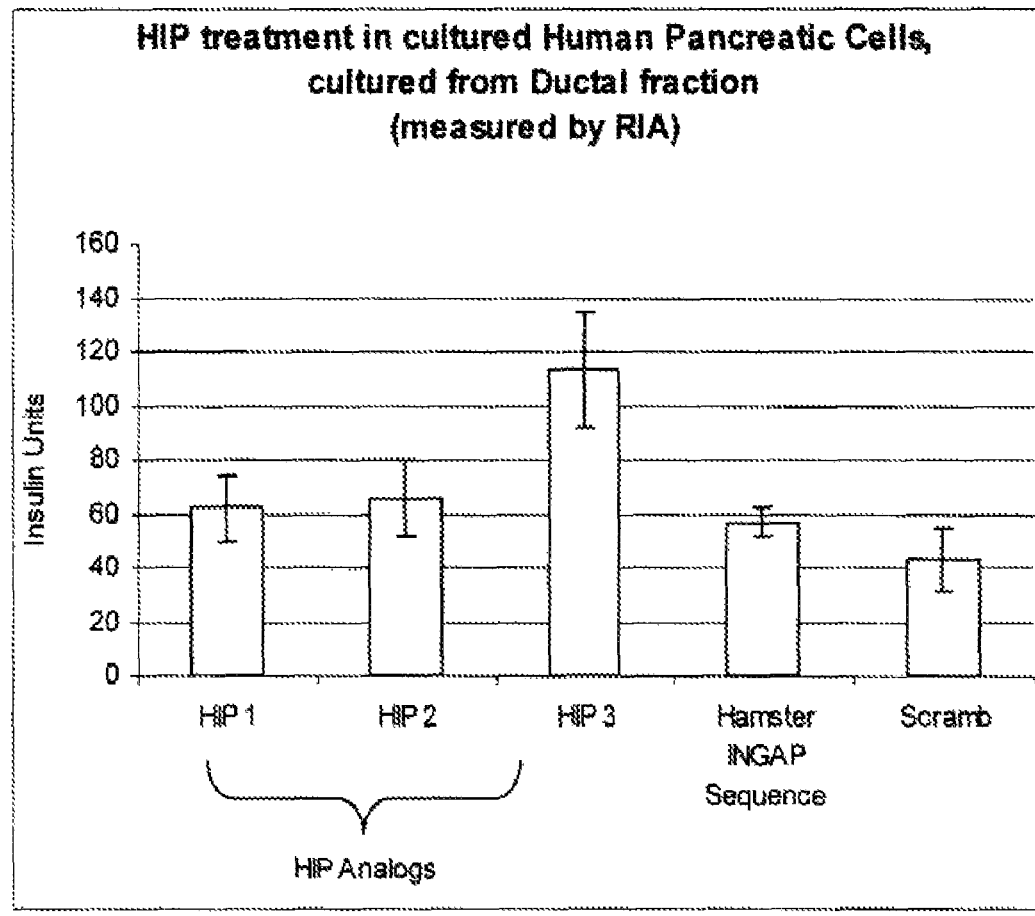
FIG. 1 is a bar graph showing increased insulin production in human pancreatic ductal tissue culture after treatment with 3.3 µM (final culture concentration of 165 nM) HIP1 (SEQ ID NO:7), HIP2 (SEQ ID NO:3), and HIP3 (SEQ ID NO:2), as compared with similar treatment with INGAP peptide and a scrambled negative control.

The invention provides Human proIslet Peptides (HIP) and analogs and derivatives thereof. Human proIslet Peptides are active fragments of the human protein regenerating islet-derived 3 alpha protein (REG3A) (NM_138937.1), also known as pancreatitis-associated protein precursor (NP_002571), incorporated herein by reference, located on chromosome 2p12. HIP induces or stimulates islet neogenesis from progenitor cells resident within the pancreas. This neogenesis agent is used to treat diseases associated with low or inadequate levels of insulin or insulin activity resulting in aberrant carbohydrate metabolism which may result from pancreatic islet dysfunction or immune destruction such as diabetes mellitus (type 1 diabetes), type 2 diabetes (non-insulin dependent diabetes mellitus and insulin requiring adult onset diabetes, diabetes in childhood and adolescence) or Latent Autoimmune Diabetes in Adults (LADA).

The invention also provides pharmaceutical compositions and therapies for the treatment of pancreatic dysfunction including type 1 and type 2 diabetes. In one embodiment, these compositions comprise HIP or an analog or derivative. In another embodiment, these compositions include HIP and other compositions that affects glucose metabolism. Included among these other compositions are agents that are involved in pancreatic islet neogenesis and agents that inhibit, block, or destroy the autoimmune cells that target pancreatic islet cells. In one embodiment, the therapies of the invention are practiced by administering a therapeutically effective dose of HIP or an analog or derivative to a mammal in need of such therapy. In another embodiment, the therapies of the invention are practiced by administering a therapeutically effective dose of HIP or an analog or derivative to a mammal in need of such therapy in combination with another hormone or compound that affects glucose metabolism, including but not limited to hormones or compounds that are involved in beta cell regeneration, satiety, and gastric emptying, such as GLP-1, GIP, GLP-1 receptor analogs, GLP-1 analogs, and Dipeptidyl Peptidase-4 Inhibitors which prevent destruction of GLP-1 and agents that inhibit, block, or destroy the autoimmune cells that target pancreatic cells. In this latter embodiment, the HIP or analog or derivative and the other hormone or agent may be administered separately or may first be admixed to provide a combination composition of the invention and administered simultaneously.

DEFINITIONS

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

As used herein, "treating" a condition or patient refers to taking steps to obtain beneficial or desired results, including clinical results. For purposes of this invention, beneficial or desired clinical results include, but are not limited to, alleviation or amelioration of one or more symptoms of diabetes, diminishment of extent of disease, delay or slowing of disease progression, amelioration, palliation or stabilization of the disease state, and other beneficial results described below. Symptoms of diabetes include low or inadequate levels of insulin or insulin activity, frequent urination, excessive thirst, extreme hunger, unusual weight loss, increased fatigue, irritability, blurry vision, genital itching, odd aches and pains, dry mouth, dry or itchy skin, impotence, vaginal yeast infections, poor healing of cuts and scrapes, excessive or unusual infections, hyperglycemia, loss of glycemic control, fluctuations in postprandial blood glucose, fluctuations in blood glucagon, fluctuations in blood triglycerides. Diabetes may be diagnosed by methods well known to one of ordinary skill in the art. For example, commonly, diabetics have a plasma blood glucose result of greater than 126 mg/dL of glucose. Pre diabetes, which may also be treated by the compositions and methods of the invention is commonly diagnosed in patients with a blood glucose result between 100 and 125 mg/dL of glucose. Other symptoms may also be used to diagnose diabetes, related diseases and conditions, and diseases and conditions affected by diminished pancreatic function.

As used herein, "reduction" of a symptom or symptoms (and grammatical equivalents of this phrase) means decreasing of the severity or frequency of the symptom(s), or elimination of the symptom(s).

As used herein, a "pathology associated with impaired pancreatic function" is one in which the pathology is associated with a diminished capacity in a subject for the pancreas of the subject to produce and/or secrete hormones and/or cytokines. Preferably this hormone or cytokine is insulin. Pathologies that are associated with impaired pancreatic function include type 1 diabetes, new onset type 1 diabetes, type 2 diabetes, latent autoimmune diabetes of adulthood, pre-diabetes, impaired fasting glucose, impaired glucose tolerance, insulin resistant syndrome, metabolic syndrome, being overweight, obesity, hyperlipidemia, hypertriglyceridemia, eating disorders and polycystic ovarian syndrome.

As used herein, "administering" or "administration of" a drug to a subject (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

As used herein, a "subject" or "patient" is a mammal, typically a human, but optionally a mammalian animal of veterinary importance, including but not limited to horses, cattle, sheep, dogs, and cats.

As used herein, a "manifestation" of a disease refers to a symptom, sign, anatomical state (e.g., lack of islet cells), physiological state (e.g., glucose level), or report (e.g., triglyceride level) characteristic of a subject with the disease.

As used herein, a "therapeutically effective amount" of a drug or agent is an amount of a drug or agent that, when administered to a subject with a disease or condition, will have the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

As used herein, a "prophylactically effective amount" of a drug is an amount of a drug that, when administered to a subject, will have the intended prophylactic effect, e.g., preventing or delaying the onset (or reoccurrence) of disease or symptoms, or reducing the likelihood of the onset (or reoccurrence) of disease or symptoms. The full prophylactic effect does not necessarily occur by administration of one dose and may occur only after administration of a series of doses. Thus, a prophylactically effective amount may be administered in one or more administrations.

As used herein, "TID", "QD" and "QHS" have their ordinary meanings of "three times a day", "once daily," and "once before bedtime", respectively.

Administration of an agent "in combination with" includes parallel administration (administration of both the agents to the patient over a period-of time, such as administration of a monoclonal antibody and a peptide hormone such as an incretin hormone or analog on alternate days for one month), co-administration (in which the agents are administered at approximately the same time, e.g., within about a few minutes to a few hours of one another), and co-formulation (in which the agents are combined or compounded into a single dosage form suitable for oral, subcutaneous or parenteral administration).

DPP-4 Inhibitors are dipeptidyl peptidase-4 inhibitors.

Hamster INGAP is a non-human islet neogenesis associated peptide.

GIP is Gastric Inhibitory Peptide, also known as Glucose-Dependent Insulinotropic Polypeptide.

GLP-1 is Glucagon-like Peptide 1.

HIP is one of the Human proIslet Peptides in purified, synthetic, or recombinant form, or incorporated into a pharmaceutical composition.

Derivatives and analogs may be full length or other than full length. Derivatives or analogs of the nucleic acids or proteins of the invention include, but are not limited to, molecules comprising regions that are substantially homologous to the nucleic acids or proteins of the invention, in various embodiments, by at least about 70%, 80%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

Islet Structures

There has been confusing nomenclature in the literature regarding the regenerative processes of the pancreas. Often the term islet "cell" has been used synonymously with beta cells and this distinction is important as new therapies for the treatment of diabetes are considered. The pancreatic islets are not cells, but are structures, each of which is composed an estimated 1000 cells of four distinct cell types: 1) Beta cells which make insulin and amylin and comprise 65-80% of the islet cells 2) Alpha cells which release glucagons and make up 15-20% of the cells 3) Delta cells making somatostatin and 4) Pancreatic polypeptide (PP) cells sometimes referred to as gamma cells. Delta and PP cells comprise less than 10% of the islet structure. Islet structures comprise only 1-2% of the pancreatic mass, yet utilize 20% of the blood supply to the pancreas and are considered one of the most vascularized cell types in the body.

There is a highly organized arrangement of the four types of cells within the islet structure. The delivery of blood flow within each islet is in a centrifugal manner with the beta cells located most centrally, and therefore receiving the core blood supply, while the alpha, delta and pancreatic polypeptide cells are positioned outside the beta cells in a lower order of perfusion.

In addition to glucose levels, which affect the beta cells, beta cells are coupled electrically to other beta cells, but not to other islet or pancreas cells. This elaborate system of communication within the islet may explain a compensatory rise in alpha cells within an islet when there is a significant decline in the beta cell mass (Kun et al., J Clin Endocrinol Metab 88: 2300-2308, 2003, Li et al., Journal of Endocrinology (2000) 165, 93-99).

Human proIslet Peptides (HIPs)

The Human proIslet Peptides (HIPs) and analogs thereof of the invention are active fragments of human REG3A or pancreatitis-associated protein precursor on chromosome 2p12. The REG3A protein from which the HIPs of the invention are derived is shown in Table 1. The domain which provides the HIPs of the invention is shown in boldface.

TABLE 1

REG3A/Pancreatitis-associated protein precursor amino acid sequence amino acid sequence.

MLPPMALPSVSWMLLSCLMLLSQVQGEEPQRELPSARIRCPKGSKAYGS

HCYALFLSPKSWTDADLACQKRPSGNLVSVLSGAEGSFVSSLVKSIGNS

YSYVWIGLHDPTQGTEPNGEGWEWSSSDVMNYFAWERNPSTISSPGHCA

SLSRSTAFLRWKDYNCNVRLPYVCKFTD (SEQ ID NO: 1)

HIP and analogs and derivatives thereof of the invention include the polypeptides shown below in Table 2 in purified, synthetic, or recombinant form, or contained in a pharmaceutical composition.

TABLE 2

Sequence of Human proIslet Peptide (HIP) and analogs

| | | |
|---|---|---|
| IGLHDPTQGTEPNGE | HIP | SEQ ID NO: 2 |
| IGLHDPTQGTEPNG | Glutamate-less HIP | SEQ ID NO: 3 |
| VWIGLHDPTQGTEPNGE | Valine-Tryp HIP Analog | SEQ ID NO: 4 |
| IGLHDP | Hexapeptide HIP | SEQ ID NO: 5 |
| WIGLHDP | Septapeptide HIP | SEQ ID NO: 6 |
| WIGLHDPTQGTEPNG | Tryp-Glutamate-less HIP | SEQ ID NO: 7 |
| WIGLHDPTQGTEPNGE | Tryp-HIP | SEQ ID NO: 19 |
| IGLHDPT | Second Septapeptide HIP | SEQ ID NO: 18 |

These peptides are the human homologues of the hamster INGAP peptide disclosed in U.S. Pat. No. 5,834,590, incorporated, herein, by reference in its entirety. This patent discloses a hamster islet neogenesis associated protein (INGAP) and associated peptides at least 15 amino acids in length. A BLAST2P alignment of human REG3A and hamster INGAP performed on the NCBI website is shown below in Table 3.

TABLE 3

```
BLAST2P alignment of REG3A (SEQ ID NO: 1) and golden
               hamster INGAP (SEQ ID NO: 8).

REG3:     1 MLPPMALPSVSWMLLSCLMLLSQVQGEEPQRELPSARIRCPKGSKAYGSHCYALFLSPKS    60
            M+ PM L  +SWMLLSCLM LS V+GEE Q++LPS+RI CP+GS AYGS+CY+L L P++
INGAP:    1 MMLPMTLCRMSWMLLSCLMFLSWVEGEESQKKLPSSRITCPQGSVAYGSYCYSLILIPQT    60

REG3:    61 WTDADLACQKRPSGNLVSVLSGAEGSFVSSLVKSIGNSYSYVWIGLHDPTQGTEPNGEGW   120
            W++A+L+CQ    SG+L  +LS  E +FVSSLVK+    +Y Y+WIGLHDP+ GT PNG GW
INGAP:   61 WSNAELSCQMHFSGHLAFLLSTGEITFVSSLVKNSLTAYQYIWIGLHDPSHGTLPNGSGW   120

REG3:   121 EWSSSDVMNYFAWERNPSTISSPGHCASLSRSTAFLRWKDYNCNVRLPYVCKF           173
            +WSSS+V+ ++ WERNPS  +  G+CA LS+ + F +W+D+NC    LPY+CKF
INGAP:  121 KWSSSNVLTFYNWERNPSIAADRGYCAVLSQKSGFQKWRDFNCENELPYICKF           173
```

In boldface in Table 3 above, is the domain in REG3A from which HIP (SEQ ID NO:2) is derived and the corresponding hamster sequence in INGAP. In U.S. Publication No. 2004/0132644, incorporated herein by reference in its entirety, an INGAP peptide shown in bold above in Table 3 is disclosed. This hamster INGAP peptide is being studied for its efficacy in islet neogenesis.

The present invention has also enabled the identification of corresponding HIP-like peptides from animals in addition to the previously known hamster INGAP, and thus, in one important aspect, provides these peptides and their analogs in substantially pure and recombinant form, as well as pharmaceutical preparations containing them, and therapeutic methods for using them to increase insulin production. While each of these HIP-like peptides from animals other than hamster are particularly suited for practicing the method of the invention in the animal or origin, those of skill in the art will recognize from this disclosure that these peptides can also be used in animals other than the animal of origin and in humans in accordance with the teachings of the invention.

Table 4, below, shows illustrative non-human HIP-like peptides provided by the present invention; the hamster INGAP sequence is shown for comparison purposes.

TABLE 4

Alignment of HIP homologous Sequences from other Mammalian Species.

| Species | Sequence | | | | | | | | | | | | | |
|---|---|---|---|---|---|---|---|---|---|---|---|---|---|---|
| Human | W | I | G | L | H | D | P | T | Q | G | T | E | P | N | G | E | (SEQ ID NO: 19) |
| Chimp | W | I | G | L | H | D | P | T | Q | G | S | E | P | D | G | G | (SEQ ID NO: 20) |
| Hamster | W | I | G | L | H | D | P | S | H | G | T | L | P | N | G | S | (SEQ ID NO: 21) |
| Mouse | W | I | G | L | H | D | P | T | M | G | Q | Q | P | N | G | G | (SEQ ID NO: 22) |
| Norway Rat | W | I | W | L | H | D | P | T | M | G | Q | Q | P | N | G | G | (SEQ ID NO: 23) |
| Cow | W | I | G | L | H | D | P | T | E | G | S | E | P | D | A | G | (SEQ ID NO: 24) |
| Dog | W | M | G | L | H | D | P | T | E | G | Y | E | P | N | A | D | (SEQ ID NO: 25) |
| Sheep | W | I | G | L | H | D | P | T | E | G | S | E | P | N | A | G | (SEQ ID NO: 26) |

The mutations shaded above in Table 4 are summarized below.
M=Methionine/I=Isoleucine both non-polar hydrophobic
ATG vs ATA SNP W=Tryptophan/G=Glycine subst: Non-polar hydrophobic/polar uncharged
T GG vs G GG SNP
S=Serine/T=Threonine both polar uncharged
T CX vs A CX Four possible SNP's with same result
L=Leucine/Q=Glutamine subst: non-polar hydrophobic/polar uncharged
CT G vs CA G One Possible SNP
E=Glutamic acid/Q Glutamine subst: polar uncharged with Acidic
G AA/GAG vs CAA/CAG Two possible SNPs
N=Asparagine/D=Aspartic acid subst: polar uncharged/acidic
A AT/A AC vs G AT/G AC Two possible SNPs=same result
G=glycine/A=Alanine subst: polar uncharged/non-polar hydrophobic
GG X vs GC X Four possible SNPs with same result The novel HIP and HIP-like peptide sequences provided by the present invention are highly homologous, reflecting the importance of the function of such peptides—to induce pancreatic islet neogenesis. This conservation of sequence, relative to that of the hamster INGAP, provides further demonstration that HIP and its analogs and derivatives, including the non-hamster HIP-like peptides shown in Table 4 above, are efficacious in stimulating islet neogenesis as provided herein.

Microarray analysis of gene expression in NOD mice has shown the upregulation of the Reg genes specifically in islet neogenesis (Vukkadapu et al, Physiol Genomics. 2005 Apr. 14; 21(2):201-11). In addition, Reg genes have been known to upregulate in late fetal development to populate the pancreas of a developing human to maintain its own glucose metabolism post partum. Hao et al, 2006, Nature Medicine 12(3): 310-6 showed that co-transplantation of fetal tissue with non-endocrine pancreatic epithelials cells (NEPECs) resulted in stimulation of new islet structures from the NEPEC population. The upregulation of Reg and therefore the abundance of HIP in the co-transplanted fetal material was likely the stimulus for this effect.

Hamster INGAP has been subject to clinical trials. While hamster INGAP has been shown to be well tolerated in Phase I and II trials, a Phase II trial had high drop out of diabetic patients due to discomfort and bruising at the hamster INGAP injection site. Little effectiveness was found for hamster INGAP in the Phase II trial as well. The HIP invention should not have the same drop out problems because they are derived from human, as opposed to hamster sequences. Further, HIP and derivatives and analogs thereof may be administered at an increased number of doses a day. The number of daily doses may be 2, 3, 4, 5, 6, 7, 8, 9 or 10. The doses may be given before meals to increase effectiveness in some patients. It is hypothesized that HIP stimulates differentiation of progenitor cells within the pancreas into new islet structures and is secreted in response to mild hyperglycemia. Administration of HIP immediately prior to meals and being present during hyperglycemia following ingestion of the meal mimics the wild type secretion schedule, which may cause more effective treatment in patients.

Despite the adverse effects shown in the Phases II hamster INGAP trials, INGAP did show some signs of effectiveness in the trials. Patients treated with 600 mg/day of hamster INGAP showed an increase in C-peptide secretion.

Also, in the 300 mg/day treatment group of the Phase II study, 22% of the patients had a >50% increase in GAD65 antibody titers. GAD65 antibody binds to lymphocytes which attack beta cells within the islets. Thus a rise in GAD65 antibody titers reflects new beta cell production associated with islet neogenesis stimulated by hamster INGAP.

Also, hemoglobin A1C fell in type 2 diabetes patients. This is correlated a decrease in glycemic exposure, and thus a lower average blood glucose. This also suggests that hamster INGAP is having some positive effect on islet function in patients, despite its adverse effects, shown in the Phase II study for hamster INGAP.

HIP analogs of the invention include any peptide comprising at least a 6 amino acid sequence from the boldface sequence shown above, i.e. SEQ ID NO:2. For example, peptide sequences of 15 amino acids or less (i.e. having 6, 7, 8, 9, 10, 11, 12, 13, or 14 amino acids) comprising any of the 6 amino acid sequences shown in Table 5 are contemplated as peptides of the invention.

TABLE 5

Embodiments of sequences comprised within HIP analogs.

| Peptide | SEQ ID NO: |
|---|---|
| IGLHDP | 5 |
| GLHDPT | 9 |
| LHDPTQ | 10 |
| HDPTQG | 11 |
| DPTQGT | 12 |
| PTQGTE | 13 |
| TQGTEP | 14 |
| QGTEPN | 15 |
| GTEPNG | 16 |
| TEPNGE | 17 |

In one embodiment, the HIP of the invention provided in purified, synthetic, or recombinant form induces pancreatic islet neogenesis and is entirely comprised of human sequence. These peptides are advantageous relative to the non-human HIP homologues, such as the hamster INGAP, because they do not contain any non-human peptide sequence. Thus, there is little chance for immune reaction when these peptides are administered to humans, as opposed to the hamster INGAP peptides.

Further, the HIP peptides of the invention may be stably stored for long periods of time. HIP peptides of the invention are stable for months when stored at 20° C. in isotonic saline.

In a specific embodiment, the derivative or analog is functionally active, i.e., capable of exhibiting one or more functional activities associated with HIP. Derivatives or analogs of HIP can be tested for the desired activity by procedures known in the art, including but not limited to, using appropriate cell lines, animal models, and clinical trials. For example, assays described in Jamal, A. M., et al. *Cell Death Differ.* 2005 July; 12(7):702-12, incorporated herein by reference in its entirety, may be used.

In particular, HIP derivatives can be made via altering HIP sequences by substitutions, insertions, or deletions that provide for functionally equivalent or improved molecules. Due to the degeneracy of nucleotide coding sequences, other DNA sequences which encode the same or a substantially similar amino acid sequence as HIP or analogs or derivatives thereof may be used in the practice of the present invention. These include, but are not limited to, nucleic acid sequences comprising all or portions of HIP that are altered by the substitution of different codons that encode a functionally equivalent amino acid residue within the sequence, thus producing a silent change. Likewise, the HIP derivatives of the invention include, but are not limited to, those containing, as a primary amino acid sequence, all or part of the amino acid sequence of HIP including altered sequences in which functionally equivalent amino acid residues are substituted for residues within the sequence resulting in a silent change. For example, one or more amino acid residues within the sequence can be substituted by another amino acid of a similar polarity that acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. HIP derivatives of the invention also include, but are not limited to, those containing, as a primary amino acid sequence, all or part of the amino acid sequence of HIP including altered sequences in which amino acid residues are substituted for residues with similar chemical properties. In a specific embodiment, 1, 2, 3, 4, or 5 amino acids are substituted.

Derivatives or analogs of HIP include, but are not limited to, those proteins which are substantially homologous to HIP or fragments thereof, or whose encoding nucleic acid is capable of hybridizing to the HIP nucleic acid sequence.

In a specific embodiment, chimeric or fusion proteins may be used in the method of the invention. As used herein, a "chimeric protein" or "fusion protein" comprises HIP or an analog or derivative thereof operatively-linked to a non-HIP or an analog or derivative thereof. Within such a fusion protein, the HIP or analog or derivative thereof can correspond to all or a portion of HIP. In one embodiment, a HIP fusion protein comprises at least one biologically-active portion of HIP. Within the fusion protein, the HIP or analog or derivative thereof and the non-HIP polypeptide are "operatively-linked", that is they are fused in-frame with one another. The non-HIP polypeptide can be fused to the N-terminus or C-terminus of the HIP or analog or derivative thereof. For example, the fusion protein may be a HIP protein containing a heterologous signal sequence at its N-terminus. In certain host cells (e.g., mammalian host cells), expression and/or secretion of HIP or an analog or derivative thereof can be increased through use of a heterologous signal sequence. In yet another example, the fusion protein is a HIP-immunoglobulin fusion protein in which the HIP sequences are fused to sequences derived from a member of the immunoglobulin protein family. The HIP-immunoglobulin fusion proteins can be incorporated into pharmaceutical compositions and administered to a subject to inhibit an immunological response according to the present invention.

HIP, an analog or derivative thereof, or a HIP-chimeric or fusion protein for use in the methods of the invention may be chemically modified for the purpose of improving bioavailability, and/or increasing efficacy, solubility and stability. For example, the protein may be covalently or non-covalently linked to albumin, transferrin or polyethylene glycol (PEG).

HIP, an or analog or derivative thereof, or a HIP-chimeric or fusion protein for use in the method of the invention can be produced by standard recombinant DNA techniques in accordance with the teachings of the invention. For example, DNA fragments coding for the different polypeptide sequences may be ligated together in-frame in accordance with conventional techniques, e.g., by employing blunt-ended or staggerended termini for ligation, restriction enzyme digestion to provide for appropriate termini, filling-in of cohesive ends as appropriate, alkaline phosphatase treatment to avoid undesirable joining, and enzymatic ligation. Furthermore, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence [see, e.g., Ausubel, et al. (eds.) CURRENT PROTOCOLS IN MOLECULAR BIOLOGY, John Wiley & Sons, (1992)]. Moreover, many expression vectors are commercially available that already encode a fusion moiety (e.g., a GST polypeptide). A HIP-encoding nucleic acid can be cloned into such an expression vector such that the fusion moiety is linked in-frame to HIP. The fusion protein can be a HIP protein fused to a His tag or epitope tag (e.g. V5) to aid in the purification and detection of the recombinant HIP, or to mask the immune response in a subject. The relatively short amino acid sequences of HIP and its analogs and derivatives make synthetic production of these valuable peptides readily practicable as well, and a variety of automated instruments for peptide synthesis are commercially available, and synthetic methods for peptide synthesis not requiring automation have long been known and can be used in accordance with the teachings herein to prepare a HIP or analog or derivative of the invention.

In some embodiments, HIP, an or analog or derivative thereof, or a HIP-chimeric or fusion protein can be modified so that it has an extended half-life in vivo using any methods known in the art. For example, Fc fragment of human IgG or inert polymer molecules such as high molecular weight polyethyleneglycol (PEG) can be attached to HIP or an analog or derivative thereof with or without a multifunctional linker either through site-specific conjugation of the PEG to the N- or C-terminus of the protein or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to HIP or an analog or derivative thereof. Unreacted PEG can be separated from HIP-PEG conjugates by size-exclusion or by ion-exchange chromatography. PEG-derivatized conjugates can be tested for in vivo efficacy using methods known to those of skill in the art.

Methods of the Invention and Agents Useful Therein
Overview of the Methods of the Invention The present invention provides HIP or HIP derivative or analog based therapies and methods for increasing insulin and other pancreatic hormone production or activity in a subject. In one embodiment, the method is practiced to treat type 1 or type 2 diabetes mellitus and related conditions in which there is a lack of or diminished insulin production in a patient resulting in aberrant glucose metabolism. The method comprises administering to that patient an agent that stimulates pancreatic islet regeneration and/or differentiation from pancreatic progenitor cells into islet structures. This agent is HIP or an analog or derivative thereof. Optionally, HIP or HIP analog or derivative is administered with the simultaneous or contemporaneous administration of an agent that inhibits the activity of and or blocks or destroys the autoimmune cells that target pancreatic islet beta cells and optionally another agent which may also stimulates pancreatic beta cell regeneration and/or result in elevation of GLP-1 or GLP-1 receptor stimulation or is a GLP-1 analog, or is a Dipeptidyl Peptidase-4 Inhibitor, which inhibits the degradation of GLP-1.

The therapeutic methods provided by the present invention address several different underlying mechanisms that result in either the absence of, or diminished or inadequate amounts of, insulin and other hormones, or which are otherwise produced in aberrant quantities. The HIP based, combination therapies provided by the present invention can restore more normal glucose metabolism, including achieving and maintaining appropriate levels of insulin, amylin, postprandial glucose, triglycerides, and glucagon levels and ameliorate the significant weight gain and increased risk for serious hypoglycemia that is associated with tight glycemic control using insulin or oral diabetic medications.

The present invention also provides single agent therapies for treating insulin deficiency, including diabetes and related conditions. These single agent therapies include methods for the administration of HIP or HIP analogs or derivatives thereof that stimulate pancreatic islet cell regeneration and/or transformation of new insulin producing islet cells from pancreatic progenitor cells located within the adult pancreas. The islet cell neogenesis resulting from such administration with HIP can be used to treat diabetes and other diseases and conditions relating to aberrant glucose regulation. In various embodiments, these methods involved the administration of such agents, including but not limited to HIP, tryptophan-HIP, glutamate-less HIP, valine-trypytophan HIP analog, hexapeptide HIP, septapeptide HIP, second septapeptide HIP or tryptophan-glutamate-less HIP, alone or in combination with an immune blocking agent and/or co administered with a GLP-1 receptor agonist, GLP-1, GLP-1 analog, or Dipeptidyl peptidase-inhibitor in the case for type 1 diabetes or HIP in combination with GLP-1 receptor agonist, GLP-1, GLP-1 analog, or dipeptidyl peptidase-inhibitor without the need for an immune blocker in the case of type 2 diabetes. Disease conditions amenable to treatment with this methodology, include, but are not limited to type 1 and 2 diabetes, where these treatments can be used to improve glycemic control, as measured by hemoglobin A1C, and to reduce bolus insulin before meals by 10-20%, with reduced fluctuations and decreased postprandial glucose, glucagon, and triglycerides. These methods can also be used to prevent progression of impaired glucose tolerance to diabetes and to prevent progression of impaired fasting glucose to progression to impaired glucose tolerance and diabetes and to reverse newly diagnosed type 2 diabetes. These methods can also be used to treat type 2 diabetes.

Exogenous injectable insulin is a therapy for patients with type 1 diabetes and other conditions in which insulin is either absent or present in diminished or inadequate amounts relative to the glucose content in the bloodstream. Insulin therapy does not treat the underlying mechanisms disease resulting in type 1 diabetes and other such conditions in which there is diminished endogenous insulin production. The therapies, methods, modalities, and treatments described herein are the first to address the many facets of the cause and complications of diabetes. The unique therapies provided by the invention encompass diverse aspects diabetology, metabolism, and immunology. These therapies include those that restore normal levels of the many different hormones, in addition to insulin, that are diminished or absent in type 1 diabetes. The methods of the invention provide for the regeneration of new insulin producing cells and optionally immuno-modulation that together serve to ameliorate, diminish, or abolish the need for insulin among patients with type 1 diabetes and other conditions associated with inadequate insulin production and secretion.

In type 1 diabetes, there are several underlying mechanisms that result in significant reduction in the production of insulin. These include autoimmune destruction of the beta cells and reduction in regeneration capacity not only within the beta cells, but an inability of progenitor cells to differentiate into new islets may be due to the altered glucose milieu. The present invention also provides combination treatment methods that are especially efficacious, because when the autoimmune response is blocked by the co-administration with HIP or a HIP analog or derivative of an immunosuppressant, the autoimmune cells that attack the pancreatic islet cells are blocked, and peptides or other compounds that stimulate regeneration of the pancreatic islet cells are administered, the patient becomes less dependent on insulin administration.

The methods of the invention can even render some patients completely free of their dependence on administered insulin for both type 1 and 2 diabetes. Other studies (see the references Levetan et al., 2002, *Diabetes* 51(supple 2):429, Levetan et al. *Diabetes* 2002. 51(suppl. 2):474, Levetan *Diabetes* 2001; 50(supple 2):2105 PO. and Levetan et al., 2003, *Diabetes Care* 26:1-8, both incorporated herein by reference) show that, when diminished hormones other than insulin are replaced, insulin requirements in type 1 patients are significantly diminished with improved glucose control. By stimulating differentiation of new insulin producing islet structures and optionally blocking the immune cells that can destroy their function, the methods of the present invention have even greater promise, because they result in sustained, endogenous production of insulin itself, and other co-secreted hormones such as amylin.

There is a demonstrated need for the therapeutic benefits provided by the present invention. There are new insulin formulations and evidence to support that intensive insulin therapy prevents deaths and reduces the rate of blindness, amputations, and kidney failure necessitating dialysis. However, intensive insulin therapy utilizing modern modalities of multiple insulin injections and continuous insulin delivery via pump therapy is associated with a two-to-three fold increased risk of serious hypoglycemia requiring assistance from another person. In a clinical study setting, despite normalization of glucose in type 1 diabetes patients by means of intravenous insulin and glucose, the standard deviation in glucose levels, both high and low, is significantly wider than non-diabetic study subjects with the same average glucose over a 24-hour period. The present invention offers an alternate means to achieve the therapeutic benefit of intensive insulin therapy without reduced iatrogenic risk, because the endogenous production of insulin stimulated by the present methods should provide more normal rates of insulin production than can not be effectively mimicked by intensive insulin therapy.

Thus, despite insulin's availability and new technologies, including new formulations of human insulin, self blood glucose monitoring systems, continuous glucose sensors and pump therapy, normal glucose control is not approximated by current therapies. Moreover, the underlying mechanisms causing type 1 diabetes are not impacted by the current therapies available for patients with type 1 diabetes and conditions in which there is no or diminished or inadequate or otherwise aberrant insulin or amylin production and dysregulation of glucagon.

The present invention provides new methods and pharmaceutical compositions for stimulating islet neogenesis, increasing insulin or other pancreatic hormone production in a patient in need thereof, and treating type 1 diabetes mellitus, type 2 diabetes mellitus and other conditions in which the lack of or diminished insulin production is a causative factor for the disease symptoms. The methods and compositions of the invention can reverse the underlying pathologic mechanisms of these disease conditions. Thus, the methods of the invention diminish, and in some cases eliminate, the need for insulin administration to patients formerly in need thereof.

In one embodiment of this method, an agent that stimulates islet regeneration and/or differentiation from pancreatic progenitor cells into insulin producing islet structures is co-administered with HIP or an analog or derivative thereof including glutamate-less HIP, tryptophan-HIP, valine-trypytophan HIP analog, hexapeptide HIP, septapeptide HIP, second septapeptide HIP, or tryptophan-glutamate-less HIP. This agent that stimulates islet regeneration and/or differentiation from pancreatic progenitor cells into insulin producing islet structures may be HIP or an analog or derivative thereof as well as long as it is different from the first administered HIP or analog or derivative thereof. Agents that be administered with HIP or during the stepwise methods of HIP usage for the treatment of type 1 and type 2 diabetes include amylin and/or an analog, such as Pramlintide, GIP, GLP-1 and/or homologous compounds and analogs, GLP-1 receptor analogs which include Exendin-4, Liraglutide (NN2211), hamster INGAP, or HIP analogs thereof, any biologically active HIP peptide and/or the Dipeptidyl Peptidase-4 inhibitors, which delay the degradation of GLP-1. The second agent may affect beta cell regeneration, gastric emptying, satiety, insulin requirements through their impacting the GLP-1 and amylin receptor sites in the pancreas, nucleus accumbens, area postrema, and gut and may be used in such an embodiment of the method, with HIP or an analog or derivative thereof from the one first administered.

One method of treating type 1 diabetes and other pathologies resulting from diminished pancreatic function, includes a five step process. These steps include: 1) Intensive Glycemic Management, 2) Achievement and maintenance of 25-hyrdroxyvitamin D levels to >40 ng/dl via oral cholecalciferol (Vitamin D3) 3) Immune Therapy, 4) HIP administration and Insulin tapering followed by discontinuation of both HIP and Insulin and 5) Repeated usage of immune modulation on a quarterly or annual basis dependent on immune therapy chosen.

Another method includes a two step process for the treatment of type 2 diabetes, obesity, overweight, insulin resistance, hyperlipidemia, hypertriglyceridemia, and eating disorders. This process includes the steps of 1) Achievement and maintenance of 25-hyrdroxyvitamin D levels to >40 ng/dl via oral cholecalciferol (Vitamin D3) and 2) Administration of HIP in combination with a GLP-1 or GLP-1 receptor agonist or GLP-1 analog or Dipeptidyl Peptidase-4 Inhibitor.

The first two steps of the five step process of treating type 1 diabetes and other pathologies resulting from diminished pancreatic function are described in more detail below. For the first step, a three-month time period prior to the administration of HIP or HIP analog or derivative administration and prior to or with the simultaneous or contemporaneous administration of an agent that inhibits the activity of and or blocks or destroys the autoimmune cells that target islet beta cells, there will be a period of tight/intense glucose optimization. This period of tight/intense glucose optimization may include multiple daily dosages of insulin administered subcutaneously or via continuous subcutaneous administration through an insulin pump and may include the administration of synthetic amylin/Pramlintide (Symlin™), which is also absent in type 1 diabetes and aberrantly secreted in type 2 diabetes. Synthetic amylin/Pramlintide (Symlin™), has been shown to reduce glycemic excursions in type 1 patients, while reducing insulin requirements before meals (Levetan. *Diabetes Care.* 2003; 26(1):1-8).

Additionally, throughout the period of tight control, immune therapy, and HIP administration, the administration of vitamin D3, cholecalciferol may be administered at a dosage of 1000-2000 IU/day. Recent studies have demonstrated that up to 54.7% of populations in the US, regardless of latitude, have low 25-hydroxyvitamin D levels (Holick, *J Clin Endorinol Metab* 2005; 90-3215-3224). Vitamin D deficiency has been demonstrated, not only to be associated with the increased risk of type 1 diabetes and seen at the onset of type 1 diagnosis, but also is commonly seen among both patients with type 1 and 2 diabetes and maintaining levels above 40 ng/ml are recommended to maintain normal immune function in those with and without diabetes (Riachy *Apoptosis.* 2006 February; 11(2):151-9. Holick. *Mayo Clin Proc.* 2006 March; 81(3):353-73, Grant. *Prog Biophys Mol. Biol.* 2006 Feb. 28; [Epub ahead of print]. DiCesar. *Diabetes Care.* 2006 January; 29(1):174, Reis. *Diabetes Metab.* 2005; 31(4 Pt 1):318-25, Pozzilli. *Horm Metab Res.* 2005; 37(11): 680-3). No adverse effects have been seen with dosages up to 10,000 IU/day (Heaney. *Am J Clin Nutr,* 204-210, Vieth. *Am J Clin Nutr.* 2001; 73:288-294). Vitamin D in dosages of 1000-2000 IU/day are continued to maintain 25-hydroxyvitamin D levels >40 ng/dl for both type 1 and 2 diabetes patients.

Step 2. Prior to the administration of the HIP or HIP analog or derivative, one of the immune modulators will be administered in its prescribed methods. Such immune modulators include immunomodulatory peptides that arrest pancreatic islet cell destruction. For example, one such immune modulator is a monoclonal antibody that can delay the progression of islet loss or slow or stop the onset of type 1 diabetes. Anti-CD3 antibodies constitute a general class of agents useful in the methods of the invention. For example, suitable anti-CD3 antibodies for purposes of the present invention include the TRX4 (Ala-Ala and ChAglyCD3) antibody under development by TolerRx and the humanized anti-CD3 antibody described in the reference Herold et al., 30 May 2002, *NEJM* 346(22):1692-1698, incorporated herein by reference. In one embodiment, the Bluestone humanized anti-CD3 antibody is delivered intravenously, 14 days per year in the dosage of 1-1.42 µg/kg on day 1, 5.67 µg/kg on day 2, 11.3 µg/kg on day 3, 22.6 µg/kg on day 4 and 45.4 µg/kg on days 5-14. These therapies would also be repeated annually following the 3-6 month usage of HIP, while insulin is being tapered as new islet cell formation occurs. During the HIP treatment phase, Vitamin D or the usage of pramlintide/Symlin™ may be continued. Following the discontinuation of HIP and insulin therapy, immune modulation will be repeated annually for the anti-CD3 antibodies, though recent study has found their efficacy to continue for as long as 24 months (Herold. *Diabetes.* 2005; 54(6):1763-9).

In another embodiment, the immuno-modulatory compound is a lysofylline or a heat shock protein that can arrest or slow islet cell destruction. Such proteins include DIAPEP277™, a heat-shock protein under development by Develogen AG (see the reference Raz et al., 2002, *Lancet* 358(9295):1749-53, incorporated herein by reference). In one embodiment, DIAPEP277™ is delivered subcutaneously by giving 1 mg in 40 mg mannitol in vegetable oil subcutaneously at baseline and at one month and then at 3 month intervals. DIAPEP277™ is continued throughout HIP therapy and following HIP therapy at quarterly intervals to protect newly generated islets from HIP therapy. In one embodiment of the combination therapy of the invention, HIP is co-administered with DIAPEP277™ as follows. The DIAPEP277™ is first administered subcutaneously at a dose of about 1 mg, about 30 days prior to the initiation of the HIP therapy. A second administration of the DIAPEP277™ is then made at the time (30 days after the first administration) of initiating the HIP therapy. The HIP therapy may be repeated as necessary, and the DIAPEP277™ is administered at a frequency of about every 3 months.

In another embodiment, hamster INGAP may be delivered by 24 hour continuous subcutaneous infusion at a dose of about 8 to 18 mg per kg of patient body weight per 24 hours. The HIP therapy may be repeated as necessary, and the DIAPEP277™ is administered at a frequency of about every 3 months.

The new HIP therapeutic methods provided by the present invention address several different underlying mechanisms that result in either the absence of, or diminished or inadequate amounts of insulin and other hormones or which are otherwise produced in aberrant quantities. The HIP based, HIP analog or derivative based, or combination therapies provided by the present invention can restore more normal glucose metabolism, including achieving and maintaining appropriate levels of insulin, amylin, postprandial glucose, triglycerides, and glucagon and ameliorate the significant weight gain and increased risk for serious hypoglycemia that is associated with tight glycemic control.

Those of skill in the art will appreciate in view of the disclosure herein that more than one agent that stimulates islet neogenesis and/or progenitor cell differentiation and/or which slows the degradation of such agents can be used in combination in the methods of the invention.

Optionally, in the practice of the methods of the invention, the HIP or analog or derivative thereof, with or without the co-administration of another selected agent, such as Symlin™/pramlintide GLP-1, a GLP-1 receptor agonist, GLP-1 agonist, or dipeptidyl-4 peptidase inhibitor, which inhibits the degradation of GLP-1, which may reduce weight, improve satiety, slow gut absorption of glucose may be used in combination with a specific agent that inhibits, blocks the activity of, or destroys autoimmune cells that target the pancreatic beta cells. Such agents include, for example, peptides, proteins, and synthetic compounds.

In one embodiment, the agent is a monoclonal antibody, a heat-shock protein, or another compound that specifically delays, prevents, or halts autoimmune destruction of the islet function. Those of skill in the art will appreciate in view of the disclosure herein that more than one agent that blocks autoimmune destruction of pancreatic islet function can be used in combination in the methods of the invention. Agents that inhibit, block the activity of, or destroy autoimmune cells that target the pancreatic islet function include: Anti CD-3 antibodies (hOKT3γ1 Ala-Ala and ChAglyCD3), Sirolimus (Rapamycin), Tacrolimus (FK506), a heat-shock protein 60 (DiaPep277) a anti-Glutamic Acid Decarboxylase 65 (GAD65) vaccine, Mycophenolate Mofetil alone or in combination with Daclizumab, the anti-CD20 agent Rituximab, Campath-1H (Anti-CD52 Antibody), lysofylline, and Vitamin D, IBC-VSO vaccine which is a synthetic, metabolically inactive form of insulin designed to prevent pancreatic beta-cell destruction, interferon-alpha. vaccination using $CD4^+$ $CD25^+$ antigen-specific regulatory T cells or a similar agent-designed to prevent pancreatic beta-cell destruction. In this latter embodiment, interferon-α vaccination using $CD4^+$ $CD25^+$ antigen-specific regulatory T cells or a similar agent is used in the combination therapy for utilizing regulatory T cells either directly or through the use of anti-CD3 immunotherapy. This embodiment, which includes an immune agent would specifically be used in type 1 diabetes patients to protect newly generated islet cells from immune attack.

Thus, the combination therapies and related methods of the invention involve the administration of HIP or analogs or derivatives thereof or co-administration of HIP or analogs or derivatives thereof with one or more agents that stimulate islet differentiation from cells in the adult pancreas with one or more agents that block autoimmune destruction of pancreatic beta cells. As used herein, an agent is "co-administered" or "used in combination" with another agent (also referred to herein as, "compound or "hormone") when the two or three agents are administered as part of the same course of therapy. In one embodiment, a first agent is first administered prior to administration of the second agent, and treatment with both is continued throughout the course of therapy. In another embodiment, the second agent is administered after the initiation or completion of the therapy involving the first agent. In other embodiments, the first agent is administered contemporaneously with the initiation of the therapy with the second agent. In another embodiment, a third agent is administered contemporaneously or before or after the administration of the first or second agent or both. In one embodiment, a therapy involving one or more agents to block or kill autoimmune cells that target pancreatic beta cells, which make insulin and amylin, is first administered prior to administration of the therapy that stimulates islet differentiation from progenitor cells in the adult pancreas. In another embodiment, treatment with the specific autoimmune blocker is continued after the cessation of treatment with agents that stimulate islet differentiation. Prior to or contemporaneously administration of immune modulating agents, there will be a three month period of intensified/tight glycemic control, which may include multiple daily injections of insulin, insulin pump therapy and usage of pramlintide/Symlin™ and vitamin D therapy in dosages of 1000-2000 IU/day to maintain a 25-hydroxyvitamin D level above 40 ng/ml.

Practice of the methods of the invention can involve multiple rounds, or "cycles," of treatment. For example, an administration of an agent that stimulates islet differentiation from progenitor cells together with an administration of an agent that blocks autoimmune cells that target pancreatic beta cells can be viewed as one cycle of the method of the invention that involves co-administration of both types of agents. Alternatively, each administration of an islet differentiation agent can be viewed as a cycle of treatment, and if an autoimmune cell blocking agent is administered, it may be administered in only a subset of such cycles, or after the last administration of the islet differentiation agent. For example, only two DIAMYD™ injections of aluminum formulated human recombinant GAD65 delivered 4 weeks apart subcutaneously to stave off further beta cell destruction in patients with autoimmune diabetes (Agardh et al., *J Diabetes Complications.* 2005; 19(4):238-46). Whereas, a single course of anti-CD3 monoclonal antibody hOKT3gamma1 (Ala-Ala) results in improvement in C-peptide responses and clinical parameters for at least 2 years after onset of type 1 diabetes the anti-CD3 antibody therapy (Herold, et al, *Diabetes.* 2005; 54(6):1763-9). Thus, depending on the selected immune blocker, the cyclicity of therapy may vary to protect new islets from immune attack. It will be understood that the above examples are for illustration only and not intended to limit the invention in any fashion. Those of skill in the art will also appreciate that, in many cases, the schedule of co-administration may differ in the first or a later therapeutic cycle for the convenience of the patient.

The combination therapies and related methods of the invention uniquely target the underlying pathologic mechanisms of type 1 diabetes with agents that regenerate new islet structures and/or differentiate pancreatic progenitor cells in combination with agents that provide targeted immune therapy. This combination therapy reverses, wholly or partially, the underlying mechanisms of type 1 diabetes, which is an autoimmune phenomenon in which anti-self antibodies attack the pancreas. Current therapies for type 1 diabetes that rely on the administration of insulin do not reverse the underlying defects in type 1 diabetes. Moreover, current immune therapies for type 1 diabetes based are based upon rejection of pancreatic beta cells and do not impact the differentiation of new fully functional islet structures containing new alpha, beta, delta, and polypeptide cells within each new islet.

Among patients with type 2 diabetes, an immune blocking agent will not be necessary since the basis of the disease is not immune destruction, although recent studies have pointed to a potentially important role of vitamin D deficiency in type 1 diabetes and a recent study found that at the time of diagnosis, more patients with type 2 diabetes are vitamin D deficient than type 1 diabetes and maintaining levels above 40 ng/ml are recommended to maintain normal immune function (Riachy *Apoptosis.* 2006 February; 11(2):151-9. Holick. *Mayo Clin Proc.* 2006 March; 81(3):353-73, Grant. *Prog Biophys Mol. Biol.* 2006 Feb. 28; [Epub ahead of print]. DiCesar. *Diabetes Care.* 2006 January; 29(1):174, Reis. *Diabetes Metab.* 2005; 31(4 Pt 1):318-25, Pozzilli. *Horm Metab Res.* 2005; 37(11):680-3). No adverse effects have been seen with dosages up to 10,000 IU/day (Heaney. *Am J Clin Nutr,* 204-210, Vieth. *Am J Clin Nutr.* 2001; 73:288-294).

The new methods provided by the present invention reverse the underlying pathologic mechanisms of type 2 diabetes and diseases and conditions resulting from decreased insulin production due to an imbalance between destruction, regeneration, and sustenance beta cells via the differentiation of new islet structures, which contain fully functional new beta cells. The methods and compounds of the invention can reduce the insulin and diabetes medication requirements of patients currently taking the drug due to having type 2 diabetes or another disease or condition and can improve glucose control in such patients. In some patients, treatment in accordance with the methods of the invention can ameliorate or obviate the need for administered insulin. The following section describes a variety of diseases and conditions that the methods and compositions of the present invention can be used to treat with therapeutic benefit.

Diseases and Conditions Amenable to Treatment

The HIP or HIP analog or derivative therapies or combination therapies of the present invention can be used to treat any mammal, including humans and animals, suffering from a disease, symptom, or condition related to a diminished production or secretion of insulin due to the loss of or diminished beta cell function or the need for greater insulin production than can be provided to the subject via differentiation of new islet structures from progenitor cells utilizing HIP compounds and methods of treatment.

Such diseases and conditions include type 1 diabetes mellitus, type 2 diabetes, pre-diabetes, impaired fasting glucose, fasting hyperinsulinemia, including but not limited to patients with type 1a diabetes patients or patients with Latent Autoimmune Diabetes of Adulthood who may manifest antibodies (anti-GAD65 antibodies, anti-islet antibodies, or anti-insulin antibodies) or those patients with type 1 diabetes with insulin deficiency without autoimmunity directed toward the beta cells (type 1b diabetes). Moreover, the present invention can be practiced with therapeutic benefit for patients newly diagnosed as having type 1 diabetes, the siblings and first degree relatives of patients with type 1 diabetes, and people with positive antibodies and other autoimmune conditions that indicate a predilection to type 1 diabetes. In one embodiment, the methods of the invention are practiced to reverse type 1 diabetes in a patient in need of such treatment.

The combination therapies and related methods and compositions of the invention can also be employed as adjunctive therapy to insulin therapy in type 1 diabetes in children and adults, to ameliorate glucose swings in patients with diabetes, and in patients with poorly controlled diabetes, hypoglycemic unawareness, and recurrent hypoglycemia in type 1 diabetes.

The HIP or HIP analog or derivative therapies and related methods and compositions of the invention can be used to treat patients having newly diagnosed type 2 diabetes, type 2 diabetes in children and adults with hyperglycemia, type 2 diabetes being concurrently treated with insulin, oral diabetic or other subcutaneous diabetic therapies, and poorly controlled type 2 diabetes. In some patients, both children and adults, the methods and compositions of the invention can reverse type 1 and 2 diabetes. The methods and compositions of the invention can also be used to treat both children and adults having atypical forms of diabetes and patients having the conditions of postprandial hyperglycemia.

The HIP or HIP analog or derivative therapies and related methods and compositions of the invention can also be used to treat patients who are children, as well, as adult patients, in need of weight loss, reduction in triglycerides, LDL cholesterol, including but not limited to achieve weight loss or treat obesity, overweight in patients having diabetes as well as those who do not have type 1 or 2 diabetes. In one embodiment, the methods and compositions of the invention are used to treat a patient having morbid obesity. In other embodiments, the methods and compositions of the invention are used to treat a patient having morbid obesity or patients having anorexia, bulimia, or other eating disorders.

The single agent therapies and related methods and compositions of the invention can also be used to treat children and adults having dysmetabolic syndrome or metabolic syndrome, as well as patients exhibiting the conditions of neuropathic pain syndromes secondary to altered glucose metabolism, and those with hypertriglyceridemia with and without diabetes, and postprandial hypertriglyceridemia. In one embodiment, these methods are practiced to treat polycystic ovarian syndrome in a patient in need of such treatment.

Other patients that can benefit from the HIP or HIP analog or derivative therapies and related methods of the invention include children and adult patients diagnosed as having conditions such as fasting hyperglycemia, pre-diabetes, impaired fasting glucose, impaired glucose tolerance, and hyperglycemic conditions generally.

The HIP or HIP analog or derivative therapies and related methods and compositions of the invention can also be used to treat patients having neuropathic pain syndromes and neuropathy, regardless of whether the patient is diagnosed as diabetic.

The HIP or HIP analog or derivative therapies and related methods and compositions of the invention can also be used to treat patients having recurrent pancreatitis or pancreatic cancer and can be used in all modalities aimed at achieving new islet structures derived from progenitor cells in the pancreas.

The following sections describe the agents useful in the methods of the invention. Those of skill in the art will appreciate, in view of the disclosure herein, that the skilled artisan may select particular agents based on the disease and condition being treated and the health and medical status of the patient.

Agents for Stimulating Pancreatic Islet Regeneration

In one embodiment of the methods of the invention, the agent that stimulates islet differentiation from pancreatic progenitor cells into insulin producing islet structures is selected from the group consisting of HIP or an analog or derivative thereof including glutamate-less HIP, tryptophan-HIP, valine-trypyophan HIP, hexapeptide HIP, septapeptide HIP, second septapeptide HIP or tryptophan-glutamate-less HIP, amylin and/or an analog, including but not limited to Pramlintide (SYMLIN™), GLP-1 receptor analogs, exendin-4 (EXENATIDE™), Liraglutide (NN2211), GLP-1, GLP-1 analogs GIP, GLP-1, hamster INGAP, other incretin-mimetic hormones, and/or similarly acting compounds and agents, and agents that extend the half-life or increase the level or activity of any of the foregoing compounds and agents, such as, for example, dipeptidyl peptidase-4 inhibitors, which delay the degradation of GLP-1. There are numerous GLP-1 mimetics that act via direct agonist activity on the GLP-1 receptors or by inhibiting the degradation of GLP-1. These agents are useful in the methods of the invention. GLP-1 mimetics can be used in conjunction with HIP and/or targeted immune therapy for the treatment of type 1 diabetes, and, as provided by the present invention, they can be used to improve glycemic control, increase satiety, delay gut glucose absorption and lead to a reversal of the underlying mechanisms resulting in type 1 diabetes. These agents and methods may prevent progression of impaired glucose tolerance in diabetes; to prevent pre-diabetes, progression of impaired fasting glucose to impaired glucose tolerance and diabetes; to reverse newly diagnosed type 2 diabetes; to treat type 2 diabetes, and to treat or prevent overweight, obesity, polycystic ovarian syndrome, and neuropathic pain syndromes.

Methods, agents, and pharmaceutical formulations useful in the practice of the present invention to achieve pancreatic islet differentiation from progenitor cells in the adult pancreas and include those described in the following references, each of which is incorporated herein by reference: Rosenberg et al., 1992, *Adv. Exp. Med. Biol.* 321: 95-104; March 1996, *Diabetologia* 39(3):256-62; July 1996, *Pancreas* 13(1):38-46; and November 2004, *Ann. Surg.* 240(5):875-84; Vinik et al., June 1997, *Horm. Metab. Res.* 29(6):278-93. The stimulation of islet regeneration or differentiation of pancreatic progenitor cells can be shown through the increased production and/or secretion of insulin in a subject.

In one embodiment of the invention, amylin or its analog, Symlin™, pramlintide is employed prior to administration or in concomitant administration with HIP, amylin may be administered prior to islet regeneration and continued through the islet regeneration period administration in accordance with the teachings of the reference Young et al., 1997, *Curr. Opin. Endocrin. Diabetes* 4: 282-290, incorporated herein by reference. In one embodiment of the invention, amylin and/or an analog, including but not limited to Pramlintide, is administered subcutaneously to optimize glycemic control prior to the initiation of HIP and may then be and used alone or in conjunction with other islet stimulating peptides, such as HIP or a HIP analog or derivative. In one embodiment, amylin or Pramlintide is dosed at 0.3-0.8 micrograms per kilogram patient weight. In one embodiment, this dose is administered subcutaneously before meals, for example, QHS and 3 AM. In one embodiment, the therapeutically effective dose is delivered subcutaneously or via an infusion device/pump and/or a transdermal, intranasal, buccal, microneedle delivery system, oral encapsulation method. In another embodiment, the therapeutically effective dose is administered utilizing sustained release formulations requiring administration by injection or other delivery method no more frequently than once a week, once every 2 weeks, or once monthly. As noted above, in some embodiments, amylin or Pramlintide is co-administered with another islet stimulating agent.

In one embodiment of the invention, a GLP-1 receptor analog, including exendin-4 or an analog is employed in the method with HIP at dosages of 5-10 mcg with meals. Exendin-4 can be formulated and administered for purposes of the present invention in accordance with the teachings of the following references, each of which is incorporated herein by reference: Alcantara et al., 1998, *Cell Biochem. Funct.* 16(1): 51-6; Dupre et al., 2004, *J. Clin. Endocrin. Metab.* 89(7): 3469-73; Edwards et al., 1999, *Diabetes* 48: 86-93; and Xu et al., 1999, *Diabetes* 48: 2270-76. In one embodiment, exendin-4 is dosed in the range of 5-10 micrograms before meals. In one embodiment, exendin-4 is administered subcutaneously alone or in conjunction with HIP and/or other islet stimulating peptides. In one embodiment, the therapeutically effective dose is administered subcutaneously. In another embodiment, delivery of exendin-4 is via transdermal, buccal, oral encapsulation methods, intranasal or microneedle delivery systems. In another embodiment, the therapeutically effective dose is contained in a sustained release formulation that requires administration no more frequently than once a week, once every 2 weeks, or once monthly. In one embodiment, exendin-4 is co-administered with HIP or another islet cell neogenesis or progenitor cell transformation agent among patients with type 1 or 2 diabetes, or those with obesity, overweight, insulin resistant syndrome, impaired fasting glucose, pre-diabetes, polycystic ovarian syndrome, the metabolic syndrome or eating disorders.

GIP and GLP-1 belong to the incretin family of growth hormones (see the references Creutzfeldt, 1979, *Diabetologia* 16: 75-85; Creutzfeldt and Ebert, 1985, *Diabetologia* 28: 565-573; Holst et al., 2001, *Scand. J. Clin. Lab. Invest. Suppl.* 234: 75-85; and Vilsboll et al., June 2003, *J. Clin. Endocrin. Metab.* 88(6):2706-13, each of which is incorporated herein by reference), and in one embodiment of the invention, an incretin hormone or analog with or without the concomitant usage of HIP is employed in the method to stimulate differentiation to islets from progenitor cells in the adult pancreas.

In one embodiment of the invention, GIP or an analog is employed with or without HIP. GIP can be formulated and administered for purposes of the present invention in accordance with the teachings of the following references, each of which is incorporated herein by reference: Andersen et al., 1978, *J. Clin. Invest.* 62: 152-161; Creutzfeldt et al., February 1980, *Diabetes* 29(2):140-5; Dupré et al., 1973, *J. Clin. Endocrin. Metab.* 37: 826-828; Ebert et al., 1980, *Clinical Gastroenterology* 9(3): 679-98; Elahi et al., 1979, *Am. J. Physiol.* 237: E185-E191, and 1994, *Regulatory Peptide* 51(1): 63-74; Krarup et al., June 1983, *J. Clin. Endocrin. Metab.* 56(6): 1306-12; Krarup et al., 1987, *Metabolism* 36(7): 677-82; Krarup et al., 1988, *Acta Med. Scand.* 223(5):437-41; Lynn et al., 2003, *FASEB* 17:19-93; Meir et al., 2002, Regulatory Peptides 107:1-3; and Nauk et al., 1993, *J. Clin. Endocrin. Metab.* 76(4): 912-7.

In one embodiment, GIP is administered intravenously or subcutaneously in combination with HIP or an analog or derivative thereof and dosed at 2-10 nanograms per kilogram patient weight to provide a 30-minute continuous infusion by either intravenous or subcutaneous delivery time beginning 3-5 minutes before meals, before bedtime, and beginning at 3 AM. In one embodiment GIP is administered subcutaneously before meals, QHS, and 3 AM. In one embodiment, GIP is administered orally or using an infusion device or a transdermal, buccal, intranasal or microneedle delivery systems. In another embodiment, a sustained release formulation requiring administration no more frequently than once every week, once every 2 weeks, or once monthly injections is employed. Suitable compositions for administering GIP in accordance with the methods of the invention are described in the reference Jones et al., 6 Nov. 1989, *Diabetes Res. Clin. Pract.* 7(4):263-9.

In one embodiment of the invention, GLP-1 or an analog, or GLP-1 receptor agonist or Dipeptidyl Peptidase-4 Inhibitor is employed in combination with HIP or an analog or derivative thereof, in the method to stimulate islet differentiation from progenitor cells, GLP-1, GLP-1 receptor agonists, GLP-1 analogs and DPP-4 inhibitors can be formulated and administered for purposes of the present invention in accordance with the teachings of the following references, each of which is incorporated herein by reference: Elahi et al., 1994, *Regulatory Peptides* 51(1): 63-74; Gutniak et al., 1994, *Diabetes Care* 17:1039-44; Kreymann et al., 1987, *Lancet* 2: 1300-1304; Larsen et al., 1996, *Diabetes* 45(Suppl. 2):233A (Abstract); Larsen et al., 2001, *Diabetes Care* 24(8): 1416-21; List et al., 2004, *Am. J. Physiol. Endocrin. Metab.* 286(6): E875-81; Lugari et al., 2000, *Horm. Metab. Res.* 32: 424-428; Marquez et al., March 1998, *Cell. Biochem. Funct.* 16(1):51-6; Meier et al., March 2004, *Critical Care Medicine* 32(3): 848-851; Meneilly et al., 2003, *Diabetes Care* 26: 2835-41; Nauk et al., 1996, *Diabetologia* 39(12):1546-53; Thorens et al., December 1995, *Diabetes Metab.* 21(5):311-8; Vilsboll et al., 2003, *J. Clin. Endocrin. Metab.* 88(6): 2706-13; Wang et al., 1997, *J. Clin. Invest.* 99: 2883-2889; and Zander et al., 2002, *Lancet* 359: 824-30.

In one embodiment, GLP-1, GLP-1 receptor agonists, GLP-1 analogs is administered subcutaneously or DPP-4 inhibitors are given orally in combination with HIP or an analog or derivative thereof and dosed in the range of 400-800 mg per day at 8-20 mg per kilogram patient weight. In one embodiment GLP-1 is administered orally or subcutaneously before meals, QHS. In one embodiment, GLP-1 is administered using a continuous subcutaneous infusion device at a rate of 1-30 ng/kilogram body weight/minute or a transdermal, buccal, or microneedle delivery system to provide a 30-minute continuous infusion by either intravenous or subcutaneous delivery time beginning 3-5 minutes before meals, before bedtime, and beginning at 3 AM. In another embodiment, a sustained release formulation requiring administration no more frequently than once every week, once every 2 weeks, or once monthly injections is employed.

In one embodiment, a non-human/hamster INGAP is administered subcutaneously in combination with HIP or an analog or derivative thereof and dosed at 5.0-20.0 milligrams per kilogram patient weight per body weight per day. In another embodiment, the hamster INGAP is administered in a continuous subcutaneous infusion over 24 hours. In another embodiment, the hamster INGAP is administered in divided dosages pr day before meals, QHS. In another embodiment, the hamster INGAP is administered using a continuous infusion by either intravenous or subcutaneous delivery device, continuous infusion via pump, transdermal patch, oral encapsulation method, microneedle delivery system to provide a consistent basal level delivery of hamster INGAP. In another embodiment, the hamster INGAP is delivered in a continuous infusion by either intravenous or subcutaneous delivery with bolus delivery before meals. In another embodiment, a sustained release formulation requiring administration no more frequently than once every week, once every 2 weeks, or once monthly injections is employed.

In one embodiment, Liraglutide (NN2211) is administered subcutaneously in combination with HIP or an analog or derivative thereof in dosages of 10-40 micrograms per kilogram body weight. In another embodiment Liraglutide is administered subcutaneously before meals, QHS, and 3 AM. In another embodiment, Liraglutide is administered using an infusion device or a transdermal, buccal, or microneedle delivery system to provide a 30-minute continuous infusion by either intravenous or subcutaneous delivery time beginning 3-5 minutes before meals, before bedtime, and beginning at 3 AM. In another embodiment, a sustained release formulation requiring administration no more frequently than once every week, once every 2 weeks, or once monthly injections is employed.

In the combination therapies of the invention, Liraglutide or NN2211 is administered at a dose of about 20 micrograms per kg of patient weight daily. This dose will provide patients the ability to reduce bolus insulin before meals by 10-20% with reduced fluctuations and decreased postprandial glucose, glucagon, and triglycerides. Administration of Liraglutide in accordance with the methods of the invention can be used to improve glycemic control, as measured, for example and without limitation, by hemoglobin A1C, in type 1 diabetes; to prevent progression of impaired glucose tolerance in diabetes; to prevent progression of impaired fasting glucose to impaired glucose tolerance and diabetes; to reverse newly diagnosed type 2 diabetes; and to treat type 2 diabetes.

In an embodiment of the combination therapy of the invention, Liraglutide or NN2211 is administered at a dose of about 20 micrograms per kg of patient weight to an adult patient in the morning, about 4 hours before food intake, and at bedtime for three consecutive weeks. For patients initiating treatment with C-peptide levels lower than about 1.0 ng/mL, C-peptide levels are monitored, and when they rise above 0.5 ng/mL, the antibody hOKT3g1 (ala-ala) is administered for 12 consecutive days.

In the combination therapies of the invention, exendin-4 or synthetic exendin-4 or another GLP-1 analog, GLP-1 receptor agonist, or Dipeptidyl Peptidase-4 Inhibitor is administered prior to meals alone or with HIP or another islet differentiation agent to improve glycemic control prior to or during the initiation of HIP therapies. Such agents, when delivered prior to meals may result in a reduction in the need for insulin of at least 20% and appropriate tapering of insulin and diabetic medications will be conducted while HIP or other islet differentiation agent is given (Levetan et al., *Diabetes Care* 2003 January; 26(1):1-8). As HIP and/or other agents are delivered in both type 1 and type 2 patients, careful taper of insulin and diabetes medications will take place to protect against hypoglycemia as new islet cells are differentiated from progenitor cells. Ultimately, insulin and diabetes medications, including HIP will be tapered off as the pancreas is repopulated with new functional islet cells. For patients initiating treatment with C-peptide levels lower than about 1.0 ng/mL, C-peptide levels are monitored, and when they rise above 0.5 ng/mL, careful monitoring and tapering of exogenous insulin dosages will occur.

Among patients with type 1 diabetes, prior to initiation of HIP and/or other peptide compounds (SYMLIN™, hamster INGAP, GLP-1, GLP-1 receptor agonists, GLP-1 analogs, DPP-4 inhibitors are used with (preceding, during, or following) immune therapy will be administered to protect newly formed islets. For example, the antibody hOKT3g1 (ala-ala) is administered for 12 consecutive days with its efficacy demonstrated following the first treatment out to 24 months, whereas a similar humanized monoclonal antibody, ChAglyCD3 may be administered for 6 consecutive days, then repeated yearly. Diamyd's GAD65 compound is delivered in two subcutaneous injections, one month apart. DIAPEP277™, a heat shock protein 60, has demonstrated success among newly diagnosed diabetes patients utilizing a subcutaneous injections of 1 mg with 40 mg mannitol in vegetable oil at study entry, 1 month, and 6 months, Based upon the immune modulator selected, the cyclicity of treatment will be determined. In another embodiment, DIAPEP277™, a heat shock protein 60 vaccine, DIAPEP277™, and IBC-VSO vaccine, which is a synthetic, metabolically inactive form of insulin designed to prevent pancreatic beta-cell destruction, interferon-alpha, or vaccination using $CD4^+CD25^+$ antigen-specific regulatory T cells or a similar agent is used in the combination therapy. In another embodiment, approaches utilizing immunomodulation including, but not limited to use of anti-CD3 immunotherapy are used, which include: Sirolimus (Rapamycin), Tacrolimus (FK506), a heat-shock protein 60 (DIAPEP277™), anti-Glutamic Acid Decarboxylase65 (GAD65) vaccine, Mycophenolate Mofetil alone or in combination with Daclizumab, the anti-CD20 agent Rituximab, Campath-1H (Anti-CD52 Antibody) and/or Vitamin D used alone or in the combination with therapy approaches to utilizing regulatory T cells either directly or through the use of anti-CD3 immunotherapy.

Agents that Inhibit, Block, or Destroy the Autoimmune Cells that Target Cells within Pancreatic Islet Structures Autoimmune cells that target pancreatic beta cells and, play a causative role in at least some of the diseases and conditions treatable in accordance with the methods of the invention. See the references Bach et al., 2001, *Ann. Rev. Immun.* 19: 131-161; Lernmark et al., *Endocrin. Metab. Clin. N. Am.* 20(3): 589-617; and Mathis et al., December 2001, *Nature* 414(6865): 792-798, each of which is incorporated herein by reference.

Prior methods of treatment involving the introduction of immune agents among patients with type 1 diabetes, protect only those islet cells which have yet been destroyed by immune attack and do not address to need to repopulate the pancreas with new islet structures with fully functionally beta cells. These methods combine generalized and specific immune modulation aimed at reducing destruction of beta cells and a methodology of differentiating new islet cells from progenitor cells within the adult pancreas.

The methods of the present invention may employ agents that specifically inhibit the activity of or block or destroy the autoimmune cells that target pancreatic beta cells that produce insulin, amylin, or glucagon. Such agents include immunomodulatory peptides that arrest pancreatic islet cell destruction. For example, one such agent is a monoclonal antibody that can delay the progression of islet cell loss or slow or stop the onset of type 1 diabetes. Anti-CD3 antibodies constitute a general class of agents useful in the methods of the invention. For example, suitable anti-CD3 antibodies for purposes of the present invention include the TRX4 (Ala-Ala and ChAglyCD3) antibody under development by TolerRx and the humanized anti-CD3 antibody described in the reference Herold et al., 30 May 2002, *NEJM* 346(22):1692-1698, incorporated herein by reference. In one embodiment, the humanized anti-CD3 antibody is delivered intravenously, 14 days per year in the dosage of 1-1.42 µg/kg on day 1, 5.67 µg/kg on day 2, 11.3 µg/kg on day 3, 22.6 µg/kg on day 4 and 45.4 µg/kg on days 5-14. These therapies may be repeated annually following the 3-6 month usage of HIP, while insulin is being tapered as new islet cell formation occurs. During the HIP treatment phase, Vitamin D and the usage of pramlintide/Symlin™ may be continued. Following the discontinuation of HIP and insulin therapy, immune modulation may be repeated annually for the anti-CD3 antibodies, though recent study has found their efficacy to continue for as long as 24 months (Herold. *Diabetes*. 2005; 54(6):1763-9).

In another embodiment, the immuno-modulatory compound is a heat shock protein that can arrest or slow islet cell destruction. Such proteins include DIAPEP277™, a heat-shock protein under development by Develogen AG (see the reference Raz et al., 2002, *Lancet* 358(9295):1749-53, incorporated herein by reference). In one embodiment, DIAPEP277™ is delivered subcutaneously by giving 1 mg in 40 mg mannitol in vegetable oil subcutaneously at baseline and at one month and then twice at 3 month intervals. In one embodiment of the combination therapy of the invention, HIP or a HIP analog or derivative is co-administered with DIAPEP277™ as follows. The DIAPEP277™ is first administered subcutaneously at a dose of about 1 mg, about 30 days prior to the initiation of the HIP or analog or derivative-based therapy. A second administration of the DIAPEP277™ is then made at the time (90 days after the first administration) of initiating the HIP or analog or derivative-based therapy.

The HIP or analog or derivative thereof may be delivered via subcutaneous injection, orally via hepatic targeted vesicle, or other liposomal agent, or via 24 hour continuous subcutaneous infusion at a dose of about 5 to 20 mg per kg of patient body weight per 24 hours so that the dosage per day is ~600-800 mg/day per patient. The HIP or analog or derivative-based therapy is continued for a 3-6 month period and monitored closely by C-peptide production. The immune therapy will be delivered cyclically based upon the immune agent selected. For example, the DIAPEP277™ is administered at 3 month intervals for a total of 6 months, and would initially be delivered 3 months prior to HIP or analog or derivative-based therapy (Raz et al., *Lancet*. 2001 Nov. 24; 358(9295):1749-53).

The immuno-modulatory agents useful in the methods of the invention can be formulated, administered, and dosed as known in the art or as described herein. Pharmaceutical formulations and additional dosing and administration protocols for practice of the methods of the invention are described below.

Additivity/Synergy

Compositions of HIP or an analog or derivative thereof, e.g., glutamate-less HIP, tryptophan-HIP, valine-trypyophan HIP, hexapeptide HIP, septapeptide HIP, second septapeptide HIP or tryptophan-glutamate-less HIP, and pharmaceutically acceptable salts and esters thereof are synergistically or additively effective to differentiate progenitor cells into new islet cells in treating diabetes or a similar disorders when combined with various other compounds. These compounds include HIP and analogs or derivatives thereof, amylin and/or an analog, including but not limited to Symlin/Pramlintide, GLP-1, GLP-1 receptor agonists, such as exendin-4, Liraglutide (NN2211), GLP-1 analogs, Dipeptidyl Peptidase-4 Inhibitors, GIP, hamster INGAP, and other incretin-mimetic hormones, and/or similarly acting compounds and agents, and agents that extend the half-life or increase the level or activity of any of the foregoing compounds and agents, such as, for example, dipeptidyl peptidase inhibitors, which delay the degradation of GLP-1, and agents that inhibit, block, or destroy the autoimmune cells that target beta cells including but not limited to: anti CD-3 antibodies (hOKT311 Ala-Ala and ChAglyCD3), Sirolimus (Rapamycin), Tacrolimus (FK506), a heat-shock protein 60 (DIAPEP277™) a anti-Glutamic Acid Decarboxylase 65 (GAD65) vaccine, Mycophenolate Mofetil alone or in combination with Daclizumab, the anti-CD20 agent Rituximab, Campath-1H (Anti-CD52 Antibody), lysofylline, and Vitamin D, IBC-VSO vaccine which is a synthetic, metabolically inactive form of insulin designed to prevent pancreatic beta-cell destruction, and interferon-α vaccination using $CD4^+CD25^+$ antigen-specific regulatory T cells or a similar agent designed to prevent pancreatic beta-cell destruction. In this last embodiment, interferon-α vaccination using $CD4^+CD25^+$ antigen-specific regulatory T cells or a similar agent is used in the combination therapy for utilizing regulatory T cells either directly or through the use of anti-CD3 immunotherapy.

Compounds such as Sirolimus (Rapamycin), Tacrolimus (FK506), TRX4 antibody, humanized anti-CD3 antibody, DYAMID™ anti-GAD65 antibody, and DIAPEP277™ are also synergistically or additively effective when added to usage of HIP or an agent to differentiate progenitor cells into new islet cells in treating diabetes or a similar disorders.

Synergy is defined as the interaction of two or more agents so that their combined effect is greater than the sum of their individual effects. For example, if the effect of drug A alone in treating a disease is 25%, and the effect of drug B alone in treating a disease is 25%, but when the two drugs are combined the effect in treating the disease is 75%, the effect of A and B is synergistic.

Additivity is defined as the interaction of two or more agents so that their combined effect is similar to the average of their individual effects. For example, if the effect of drug A alone in treating a disease is 25%, and the effect of drug B alone in treating a disease is 25%, but when the two drugs are combined the effect in treating the disease is about 50% or at least greater than 25%, the effect of A and B is additive.

An improvement in a drug therapeutic regimen can be obtained by the combined administration of two agents having therapeutic effect, if the interaction of the two or more agents is such that their combined effect reduces the incidence of adverse event (AE) of either or both agents used in the co-therapy. This reduction in the incidence of adverse effects can be a result of, e.g., administration of lower dosages of either or both agent used in the co-therapy. For example, if the effect of drug A alone is 25% and has an adverse event incidence of 45% when used at the labeled dose; and the effect of drug B alone is 25% and has an adverse event incidence of 30% when used at the labeled dose, but when the two drugs are combined at lower than labeled doses of each, if the overall effect is 35% and the adverse incidence rate is 20%, there is an improvement in the drug therapeutic regimen. The combination therapies provided by the present invention include those exhibiting such improvements.

Pharmaceutical Compositions, Dosing and Administration

Dosing and administration of the agents useful in the methods of the invention as described herein provide accelerated islet differentiation from adult progenitor cells to optimize an individual's ability to secrete insulin from endogenous, newly formed islet structures with used in conjunction with immune therapy or therapies, which give the lowest toxicity while providing protection of the new islets from destruction. Pharmaceutical compositions of the invention provide for kinetic delivery of these agents, ease of delivery, and enhanced efficacy.

In one embodiment, HIP peptide would be dosed subcutaneously, between about 20-2000 mg, (0.02857 to 285.7 mg/kg) four times daily, pre-prandially, before each meal and a dose at bedtime. In another embodiment, HIP peptide is dosed at about 200 mg (2.857 mg/kg) four times daily, pre-prandially, before each meal and a dose at bedtime.

Preferably HIP peptide would be dosed at 10-15 mg/kg delivered in four separate subcutaneous injections for a total of approximately 800 mg/day total per day.

HIP Peptide may be administered as few times as once daily and as many times as 20 times daily or by continuous infusion.

The agents useful in the methods of the invention can be administered by a variety of routes. Known agents useful in the methods of the invention can be administered by routes and using pharmaceutical formulations previously developed for other indications. Such delivery routes include, at least for most known agents, oral delivery, targeted and untargeted liposomal drug delivery systems for oral or subcutaneous delivery, which may include the hepatic-directed vesicle (AMDG/SDG) attached to HIP or compounds used in the methodologies described herein, topical delivery, including micelle and nanosphere topical delivery systems, subcutaneous delivery including pump-assisted continuous infusion by either intravenous or subcutaneous delivery and disposable micro-pumps and micro-needles (including but not limited to those available from Animas Corp.), and buccal delivery.

The particular route of administration and pharmaceutical formulation of an agent used in the practice of the methods of the invention will be selected by the practitioner based on a patient's disease or condition being treated and the agent employed. A wide variety of pharmaceutical compositions can be employed in the methods of the invention. In some embodiments, extended use preparations can be used for ease of administration and increased efficacy.

In one embodiment, one or more of the agents employed in the method is formulated as a micelle. Often, ease of administration is best achieved by oral delivery. While small molecule pharmaceutical agents can often be readily formulated for oral delivery, peptide and protein-based pharmaceutical agents can be more difficult to formulate for oral delivery. However, suitable formulation technology exists, and in one important aspect, the present invention provides pharmaceutical compositions of proteins and peptides formulated for oral delivery. In one embodiment, the pharmaceutical compositions useful in the methods of the invention suitable for oral delivery are formulated generally in accordance with known TECHNOSPHERE™ technology developed by MannKind Corp., ELIGEN® Technology developed by Emisphere, a nasal delivery systems developed by Nastech, an oral liposome with specificity to the liver (HDV) developed by AMDG/SDG).

Other oral delivery and encapsulation technology suitable for use in making the pharmaceutical compositions of the invention includes the hepatic delivery vesicle (HDV). Pancreatic delivery vesicle (PDV) technology has been proposed by CureDM to SDG/AMDG for potential usage in delivery of compounds described in the methods herein. HDV technology can be used to deliver compounds in the methodology herein including HIP (Davis et al., 2001, *J. Diabetes Comp.* 15(5): 227-33) and GLP-1 directly to the liver. PDV technology provides liposomes with a conjugated protein or other molecule on its surface that directs an agent, such as a peptide that stimulates islet cell neogenesis, directly to the pancreas.

Agents that can be formulated for oral delivery and employed in the methods of the invention include HIP or an analog or derivative thereof including glutamate-less HIP, tryptophan-HIP, valine-trypyophan HIP, hexapeptide HIP, septapeptide HIP, second septapeptide HIP or tryptophan-glutamate-less HIP, SYMLIN™/pramlintide, Exendin-4, Liraglutide (NN2211), GLP-1 receptor agonists, GLP-1, GLP-1 analogs, hamster INGAP and its analogs, GIP, Dipeptydyl peptidase-4 inhibitors and peptide and proteins or non-peptidic mimetics with similar action or homology to the preceding agents used with monoclonal antibodies and other specific and general immune agents designed to delay the progression of beta cell loss or prevent the onset of type 1 diabetes in both children and adults, including, but not limited to anti CD-3 antibodies (hOKT3γ1(Ala-Ala and ChAg-lyCD3) that target the immune response and specifically block the T-lymphocytes that cause islet cell death in type 1 diabetes, as well as, Sirolimus (Rapamycin), Tacrolimus (FK506), a heat-shock protein 60 (DIAPEP277™) an anti-Glutamic Acid Decarboxylase 65 (GAD65) vaccine, Mycophenolate Mofetil alone or in combination with Daclizumab, the anti-CD20 agent, Rituximab, Campath-1H (Anti-CD52 Antibody), lysofylline, Vitamin D, IBC-VSO vaccine which is a synthetic, metabolically inactive form of insulin designed to prevent pancreatic beta-cell destruction, interferon-alpha. vaccination using $CD4^+CD25^+$ antigen-specific regulatory T cells or a similar agent is used in the combination therapy approaches to utilizing regulatory T cells either directly or through the use of immunotherapy to arrest the destruction of insulin-producing cells.

Kits

The invention further relates to kits for treating patients having type 1 or type 2 diabetes or other glucose metabolism disorders in children and adults including pre-diabetes, impaired fasting glucose, insulin resistant syndromes, the metabolic syndrome, obesity, overweight, polycysistic ovarian syndrome, hyperlipidemia, hypertriglyceridemia comprising one or more therapeutically effective methods of HIP or an analog or derivative modes of treatment thereof (e.g., tryptophan HIP, glutamate-less HIP, valine-trypyophan HIP, hexapeptide HIP, septapeptide HIP, second septapeptide HIP or tryptophan-glutamate-less HIP). Optionally, the kit may also contain other agents (e.g. SYMLIN™/pramlintide, exendin-4, GIP, GLP-1 receptor agonists, Liraglutide (NN2211), Exendin-4, GLP-1 analogs, hamster INGAP, or a dipeptidyl peptidase inhibitor) and/or agents that inhibit, block, or destroy the autoimmune cells that target pancreatic islet cells including, but not limited to but not limited to anti CD-3 antibodies (hOKT3γ1(Ala-Ala and ChAglyCD3) that target the immune response and specifically block the T-lymphocytes that cause islet cell death in type 1 diabetes, as well as, Sirolimus (Rapamycin), Tacrolimus (FK506), a heat-shock protein 60 (DiaPep277) an anti-Glutamic Acid Decarboxylase 65 (GAD65) vaccine, Mycophenolate Mofetil alone or in combination with Daclizumab, the anti-CD20 agent, Rituximab, Campath-1H (Anti-CD52 Antibody), lysofylline, Vitamin D, IBC-VSO vaccine which is a synthetic, metabolically inactive form of insulin designed to prevent pancreatic beta-cell destruction, interferon-alpha. vaccination using $CD4^+CD25^+$ antigen-specific regulatory T cells or a similar agent is used in the combination therapy approaches to utilizing regulatory T cells either directly or through the use of immunotherapy to arrest the destruction of insulin-producing cells, either in the same or separate packaging, and instructions for its use.

Antibodies to HIP and Analogs or Derivatives Thereof.

In various embodiments, monoclonal or polyclonal antibodies specific to HIP or analogs or derivatives thereof can be used in immunoassays to measure the amount of HIP or analogs or derivatives thereof or used in immunoaffinity purification of a HIP or analogs or derivatives thereof. A Hopp & Woods hydrophilic analysis (see Hopp & Woods, Proc. Natl. Acad. Sci. U.S.A. 78:3824-3828 (1981) can be used to identify hydrophilic regions of a protein, and to identify potential epitopes of a HIP or analogs or derivatives thereof.

The antibodies that immunospecifically bind to an HIP or analogs or derivatives thereof can be produced by any method known in the art for the synthesis of antibodies, in particular, by chemical synthesis or preferably, by recombinant expression techniques. (See, e.g., U.S. Publication No. 2005/0084449, which is incorporated herein in its entirety).

Polyclonal antibodies immunospecific for HIP or analogs or derivatives thereof can be produced by various procedures well-known in the art. For example, HIP or analogs or derivatives thereof can be administered to various host animals, including, but not limited to, rabbits, mice, and rats, to induce the production of sera containing polyclonal antibodies specific for HIP or analogs or derivatives thereof. Various adjuvants may be used to increase the immunological response, depending on the host species, including but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art, including the use of hybridoma, recombinant, and phage display technologies, or a combination thereof. For example, monoclonal antibodies can be produced using hybridoma techniques, including those known in the art and taught, for example, in Harlow et al., Antibodies: A Laboratory Manual, (Cold Spring Harbor Laboratory Press, 2nd ed. 1988); and Hammerling et al., in: Monoclonal Antibodies and T Cell Hybridomas 563 681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a non-murine antigen, and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

The present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with a non-murine antigen with myeloma cells and then screening the hybridomas resulting from the fusion for hybridoma clones that secrete an antibody able to bind to the antigen.

Antibody fragments which recognize specific particular epitopes may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in *E. coli*, and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; International application No. PCT/GB91/O1 134; International publication Nos. WO 90/02809; WO 91/10737; WO 92/01047; WO 92/18619; WO 93/11236; WO 95/15982; WO 95/20401; and WO97/13844; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

As described in the above references, after phage selection, the antibody coding regions from the phage can be isolated and used to generate whole antibodies or any other desired antigen binding fragment, and expressed in any desired host, including mammalian cells, insect cells, plant cells, yeast, and bacteria, e.g., as described below. Techniques to produce Fab, Fab' and F(ab')2 fragments recombinantly can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. Preferably, the vectors for expressing the VH or VL domains comprise an EF-1α promoter, a secretion signal, a cloning site for the variable domain, constant domains, and a selection marker such as neomycin. The VH and VL domains may also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use humanized antibodies or chimeric antibodies. Human antibodies can be made by a variety of methods known in the art including phage display methods described above using antibody libraries derived from human immunoglobulin sequences. See also U.S. Pat. Nos. 4,444,887 and 4,716,111; and International publication Nos. WO 98/46645, WO 98/50433, WO 98/24893, WO98/16654, WO 96/34096, WO 96/33735, and WO 91/10741.

A chimeric antibody is a molecule in which different portions of the antibody are derived from different immunoglobulin molecules. Methods for producing chimeric antibodies are known in the art. See e.g., Morrison, 1985, Science 229: 1202; Oi et al., 1986, BioTechniques 4:214; Gillies et al., 1989, J. Immunol. Methods 125:191-202; and U.S. Pat. Nos. 5,807,715; 4,816,567; 4,816,397; and 6,311,415.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non human immunoglobulin. A humanized antibody comprises substantially all of at least one, and typically two, variable domains (Fab, Fab', F(ab')2, Fabc, Fv) in which all or substantially all of the CDR regions correspond to those of a non human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework region (FR) and CDR sequences, more often 90%, and most preferably greater than 95%. Humanized antibody can be produced using variety of techniques known in the art, including but not limited to, CDR grafting (European Patent No. EP 239,400; International Publication No. WO 91/09967; and U.S. Pat. Nos. 5,225,539; 5,530,101; and 5,585,089), veneering or resurfacing (European Patent Nos. EP 592,106 and EP 519,596; Padlan, 1991, Molecular Immunology 28(4/5):489 498; Studnicka et al., 1994, Protein Engineering 7(6):805 814; and Roguska et al., 1994, PNAS 91:969 973), chain shuffling (U.S. Pat. No. 5,565,332), and techniques disclosed in, e.g., U.S. Pat. No. 6,407,213; U.S. Pat. No. 5,766,886; WO 9317105; Tan et al., J. Immunol. 169:1119-25 (2002); Caldas et al., Protein Eng. 13(5):353-60 (2000); Morea et al., Methods 20(3):267-79 (2000); Baca et al., J. Biol. Chem. 272(16):10678-84 (1997); Roguska et al., Protein Eng. 9(10):895-904 (1996); Couto et al., Cancer Res. 55 (23 Supp):5973s-5977s (1995); Couto et al., Cancer Res. 55(8):1717-22 (1995); Sandhu J S, Gene 150(2):409-10 (1994); and Pedersen et al., J. Mol. Biol. 235(3):959-73 (1994). Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323).

Methods of Preparing HIP and Analogs or Derivatives Thereof

Any techniques known in the art can be used in purifying HIP or an analog or derivative thereof, including but not limited to, separation by precipitation, separation by adsorption (e.g., column chromatography, membrane adsorbents, radial flow columns, batch adsorption, high-performance liquid chromatography, ion exchange chromatography, inorganic adsorbents, hydrophobic adsorbents, immobilized metal affinity chromatography, affinity chromatography), or separation in solution (e.g., gel filtration, electrophoresis, liquid phase partitioning, detergent partitioning, organic solvent extraction, and ultrafiltration). See e.g., Scopes, PROTEIN PURIFICATION, PRINCIPLES AND PRACTICE, 3rd ed., Springer (1994). During the purification, the biological activity of HIP or an analog or derivative thereof may be monitored by one or more in vitro or in vivo assays. The purity of HIP or an analog or derivative thereof can be assayed by any methods known in the art, such as but not limited to, gel electrophoresis. See Scopes, supra. In some embodiments, HIP or an analog or derivative thereof employed in a composition of the invention can be in the range of 80 to 100 percent of the total mg protein, or at least 80%, at least 85%, at least 90%, at least 95%, or at least 98% of the total mg protein. In one embodiment, HIP or an analog or derivative thereof employed in a composition of the invention is at least 99% of the total protein. In another embodiment, HIP or an analog or derivative thereof is purified to apparent homogeneity, as assayed, e.g., by sodium dodecyl sulfate polyacrylamide gel electrophoresis.

Methods known in the art can be utilized to produce HIP or an analog or derivative thereof recombinantly. A nucleic acid sequence encoding a HIP or an analog or derivative thereof can be inserted into an expression vector for propagation and expression in host cells.

An expression construct, as used herein, refers to a nucleic acid sequence encoding a HIP or an analog or derivative thereof operably associated with one or more regulatory regions that enable expression of a HIP or an analog or derivative thereof in an appropriate host cell. "Operably-associated" refers to an association in which the regulatory regions and the HIP or an analog or derivative thereof to be expressed are joined and positioned in such a way as to permit transcription, and ultimately, translation.

The regulatory regions that are necessary for transcription of HIP or an analog or derivative thereof can be provided by the expression vector. A translation initiation codon (ATG) may also be provided if a HIP or an analog or derivative thereof gene sequence lacking its cognate initiation codon is to be expressed. In a compatible host-construct system, cellular transcriptional factors, such as RNA polymerase, will bind to the regulatory regions on the expression construct to effect transcription of the HIP sequence in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

In order to attach DNA sequences with regulatory functions, such as promoters, to a HIP or an analog or derivative thereof gene sequence or to insert a HIP or an analog or derivative thereof gene sequence into the cloning site of a vector, linkers or adapters providing the appropriate compatible restriction sites may be ligated to the ends of the cDNAs by techniques well known in the art (see e.g., Wu et al., 1987, Methods in Enzymol, 152:343-349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA using PCR with primers containing the desired restriction enzyme site.

An expression construct comprising a HIP or an analog or derivative thereof sequence operably associated with regulatory regions can be directly introduced into appropriate host cells for expression and production of a HIP or an analog or derivative thereof without further cloning. See, e.g., U.S. Pat. No. 5,580,859. The expression constructs can also contain DNA sequences that facilitate integration of a HIP or an analog or derivative thereof sequence into the genome of the host cell, e.g., via homologous recombination. In this instance, it is not necessary to employ an expression vector comprising a replication origin suitable for appropriate host cells to propagate and express HIP or an analog or derivative thereof in the host cells.

A variety of expression vectors may be used, including but are not limited to, plasmids, cosmids, phage, phagemids or modified viruses. Such host-expression systems represent vehicles by which the coding sequences of a HIP or an analog or derivative thereof gene may be produced and subsequently purified, but also represent cells which may, when transformed or transfected with the appropriate nucleotide coding sequences, express HIP or an analog or derivative thereof in situ. These include, but are not limited to, microorganisms such as bacteria (e.g., *E. coli* and *B. subtilis*) transformed with recombinant bacteriophage DNA, plasmid DNA or cosmid DNA expression vectors containing HIP or an analog or derivative thereof coding sequences; yeast (e.g., *Saccharomyces, Pichia*) transformed with recombinant expression vectors containing HIP or an analog or derivative thereof coding sequences; insect cell systems infected with recombinant virus expression vectors (e.g., baculovirus) containing HIP or an analog or derivative thereof coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing HIP or an analog or derivative thereof coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli* and eukaryotic cells are used for the expression of a recombinant HIP or an analog or derivative thereof. For example, mammalian cells such as Chinese hamster ovary cells (CHO) can be used with a vector bearing promoter element from major intermediate early gene of cytomegalovirus for effective expression of a HIP or an analog or derivative thereof sequence (Foecking et al., 1986, Gene 45:101; and Cockett et al., 1990, Bio/Technology 8:2).

In bacterial systems, a number of expression vectors may be advantageously selected depending upon the use intended for the HIP or an analog or derivative thereof being expressed. For example, when a large quantity of a HIP or an analog or derivative thereof is to be produced, for the generation of pharmaceutical compositions of a HIP or an analog or derivative thereof, vectors that direct the expression of high levels of fusion protein products that are readily purified may be desirable. Vectors include, but are not limited to, the *E. coli* expression vector pCR2.1 TOPO (Invitrogen); pIN vectors (Inouye & Inouye, 1985, Nucleic Acids Res. 13:3101-3109; Van Heeke & Schuster, 1989, J. Biol. Chem. 24:5503-5509), and the like. Series of vectors like pFLAG (Sigma), pMAL (NEB), and pET (Novagen) may also be used to express the foreign proteins as fusion proteins with FLAG peptide, malE-, or CBD-protein. These recombinant proteins may be directed into periplasmic space for correct folding and maturation. The fused part can be used for affinity purification of the expressed protein. Presence of cleavage sites for specific proteases like enterokinase allows one to cleave off the HIP or an analog or derivative thereof. The pGEX vectors may also be used to express foreign proteins as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, many vectors to express foreign genes can be used, e.g., *Autographa californica* nuclear polyhedrosis virus (AcNPV) can be used as a vector to express foreign genes. The virus grows in cells like *Spodoptera frugiperda* cells. A HIP or an analog or derivative thereof coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, a HIP or an analog or derivative thereof coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing HIP or an analog or derivative thereof in infected hosts (see, e.g., Logan & Shenk, 1984, Proc. Natl. Acad. Sci. USA 8 1:355-359). Specific initiation signals may also be required for efficient translation of inserted HIP or an analog or derivative thereof coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, and the like (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript and post-translational modification of the gene product, e.g., glycosylation and phosphorylation of the gene product, may be used. Such mammalian host cells include, but are not limited to, PC12, CHO, VERY, BHK, HeLa, COS, MDCK, 293, 3T3, W138, BT483, Hs578T, HTB2, BT2O and T47D, NS0 (a murine myeloma cell line that does not endogenously produce any immunoglobulin chains), CRL7O3O, and HsS78Bst cells. Expression in a bacterial or yeast system can be used if post-translational modifications are found to be non-essential for a desired activity of HIP or an analog or derivative thereof.

For long-term, high-yield production of properly processed HIP or an analog or derivative thereof, stable expression in cells is preferred. Cell lines that stably express HIP or an analog or derivative thereof may be engineered by using a vector that contains a selectable marker. By way of example but not limitation, following the introduction of the expression constructs, engineered cells may be allowed to grow for 1-2 days in an enriched media, and then are switched to a selective media. The selectable marker in the expression construct confers resistance to the selection and may, depending on the vector construct and host cell employed, allow cells to stably integrate the expression construct into their chromosomes and to grow in culture and to be expanded into cell lines. Such cells can be cultured for a long period of time while HIP or an analog or derivative thereof is expressed continuously.

A number of selection systems may be used, including but not limited to, antibiotic resistance (markers like Neo, which confers resistance to geneticine, or G-418 (Wu and Wu, 1991, Biotherapy 3:87-95; Tolstoshev, 1993, Ann Rev. Pharmacol. Toxicol. 32:573-596; Mulligan, 1993, Science 260:926-932; and Morgan and Anderson, 1993, Ann. Rev. Biochem. 62: 191-217; May, 1993, TIB TECH 11(5):155-2 15); Zeo, for resistance to Zeocin; and Bsd, for resistance to blasticidin); antimetabolite resistance (markers like Dhfr, which confers resistance to methotrexate, Wigler et al., 1980, Natl. Acad. Sci. USA 77:357; and O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); and hygro, which confers resistance to hygromycin (Santerre et al., 1984, Gene 30:147). In addition, mutant cell lines including, but not limited to, tk–, hgprt– or aprt– cells, can be used in combination with vectors bearing the corresponding genes for thymidine kinase, hypoxanthine, guanine- or adenine phosphoribosyl-transferase. Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); Chapters 12 and 13, Dracopoli et al. (eds), of Current Protocols in Human Genetics, John Wiley & Sons, NY (1994); and Colberre-Garapin et al., 1981, J. Mol. Biol. 150: 1.

The recombinant cells may be cultured under standard conditions of temperature, incubation time, optical density and media composition. However, conditions for growth of recombinant cells may be different from those for expression of HIP or an analog or derivative thereof. Modified culture conditions and media may also be used to enhance production of HIP or an analog or derivative thereof. Any techniques known in the art may be applied to establish the optimal conditions for producing HIP or an analog or derivative thereof.

An alternative to producing HIP or a fragment thereof by recombinant techniques or purification from natural sources is peptide synthesis. For example, an entire HIP or an analog or derivative thereof, or a protein corresponding to a portion of HIP or an analog or derivative thereof, can be synthesized by use of a peptide synthesizer. Conventional peptide synthesis or other synthetic protocols well known in the art may be used.

Proteins having the amino acid sequence of HIP or an analog or derivative thereof or a portion thereof may be synthesized by solid-phase peptide synthesis using procedures similar to those described by Merrifield, 1963, J. Am. Chem. Soc., 85:2149. During synthesis, N-α-protected amino acids having protected side chains are added stepwise to a growing polypeptide chain linked by its C-terminal and to an insoluble polymeric support, i.e., polystyrene beads. The proteins are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile. Details of appropriate chemistries, resins, protecting groups, protected amino acids and reagents are well known in the art and so are not discussed in detail herein (See, Atherton et al., 1989, Solid Phase Peptide Synthesis: A Practical Approach, IRL Press, and Bodanszky, 1993, Peptide Chemistry, A Practical Textbook, 2nd Ed., Springer-Verlag).

Purification of the resulting HIP or an analog or derivative thereof is accomplished using conventional procedures, such as preparative HPLC using gel permeation, partition and/or ion exchange chromatography. The choice of appropriate matrices and buffers are well known in the art and so are not described in detail herein.

With the foregoing detailed description of the reagents and methods of the invention, the following Examples are provided to illustrate various aspects of the invention.

Example 1

HIPs Cause an Increase in Insulin Production In Vitro in Human Pancreatic Ductal Tissue Culture and Human Islet Tissue Cultures Human pancreatic islet and progenitor fractions were cultured over 10 days, according to standard protocol. Briefly, pancreata from adult human cadaveric organ donors were obtained through the local organ procurement organization. Islets were isolated according to established protocols described by Bonner-Weir and Jamal. (Bonner-Weir et al., *Pediatric Diabetes:* 2004; 5(Suppl 2):16-22. Jamal et al., *Cell Death Differ.* 2005 July; 12(7):702-12).

Following removal of the organ, cold ischemia time was no more than 8 hours prior to islet isolation. The main pancreatic duct was cannulated and perfused with Liberase HI (Roche Diagnostics). The perfused organ was placed in a closed system (Ricordi Apparatus) and heated to 37° C. to activate the enzyme blend. Following the appearance of free islets in samples, the system was cooled and free tissues were collected and washed. Tissues were applied to a continuous density gradient created using Ficoll (Biochrom KG) in a cell processor (COBE). Free islets with diameters ranging from 75 to 400 µm, determined to be greater than 90% pure by staining with dithizone (Sigma) a zinc chelator, were collected and washed. IHC to detect the presence of amylase and cytokeratin was negative, consistent with the absence of progenitor and exocrine tissue. The progenitor fraction from this separation was also collected for culture.

Isolated islets were embedded in a type 1 collagen matrix at a density of 2000 islet equivalents/25 cm$^2$ and cultured in DMEM/F12 containing 10% FBS, 1 µM dexamethasone, 10 ng/ml EGF, 24 mU/ml insulin and 100 ng/ml cholera toxin. Medium was changed every other day. On day 10, culture was continued in the above medium, without the cholera toxin, with neogenic agents and inhibitors at the final concentrations listed below. Medium was changed every other day. Collagen-embedded cultures were harvested by incubating with 0.25 g/L collagenase XI (Sigma) for 30 minutes at 37° C.

After culture the human pancreatic islet and progenitor fractions were then treated in a blinded study with one of three HIPS: SEQ ID NOs: 7, 3 or 2, the hamster INGAP sequence as a positive control (IGLHDPSHGTLPNGS (SEQ ID NO:27)) or a scrambled peptide sequence that was synthesized by Bachem BioScience (95% pure, research grade) (DGGTPQPGNWIELTH (SEQ ID NO:28)). Duplicate cultures were treated on Day 10 and Day 12 and then lysed for detection of insulin content on day 14. During 10 day culture, the insulin production decreases to negligible amounts and, after treatment with peptides, insulin is produced again.

Figure 2:
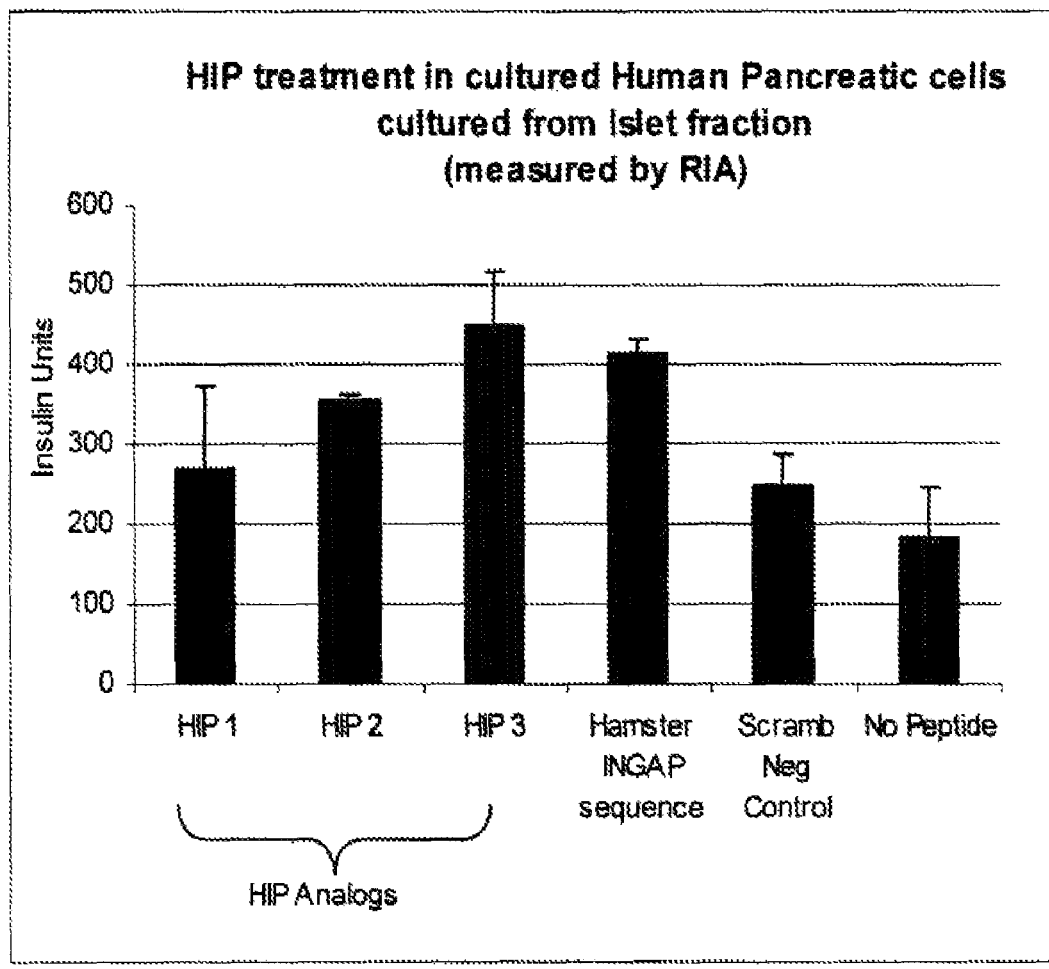
FIG. 2 is a bar graph showing increased insulin production in human pancreatic islet tissue after treatment with 1 mM for a final culture concentration of 500 nM HIP1 (SEQ ID NO:7), HIP2 (SEQ ID NO:3), and HIP3 (SEQ ID NO:2), as compared with similar treatment with INGAP peptide and a scrambled negative control.
Figure 3:
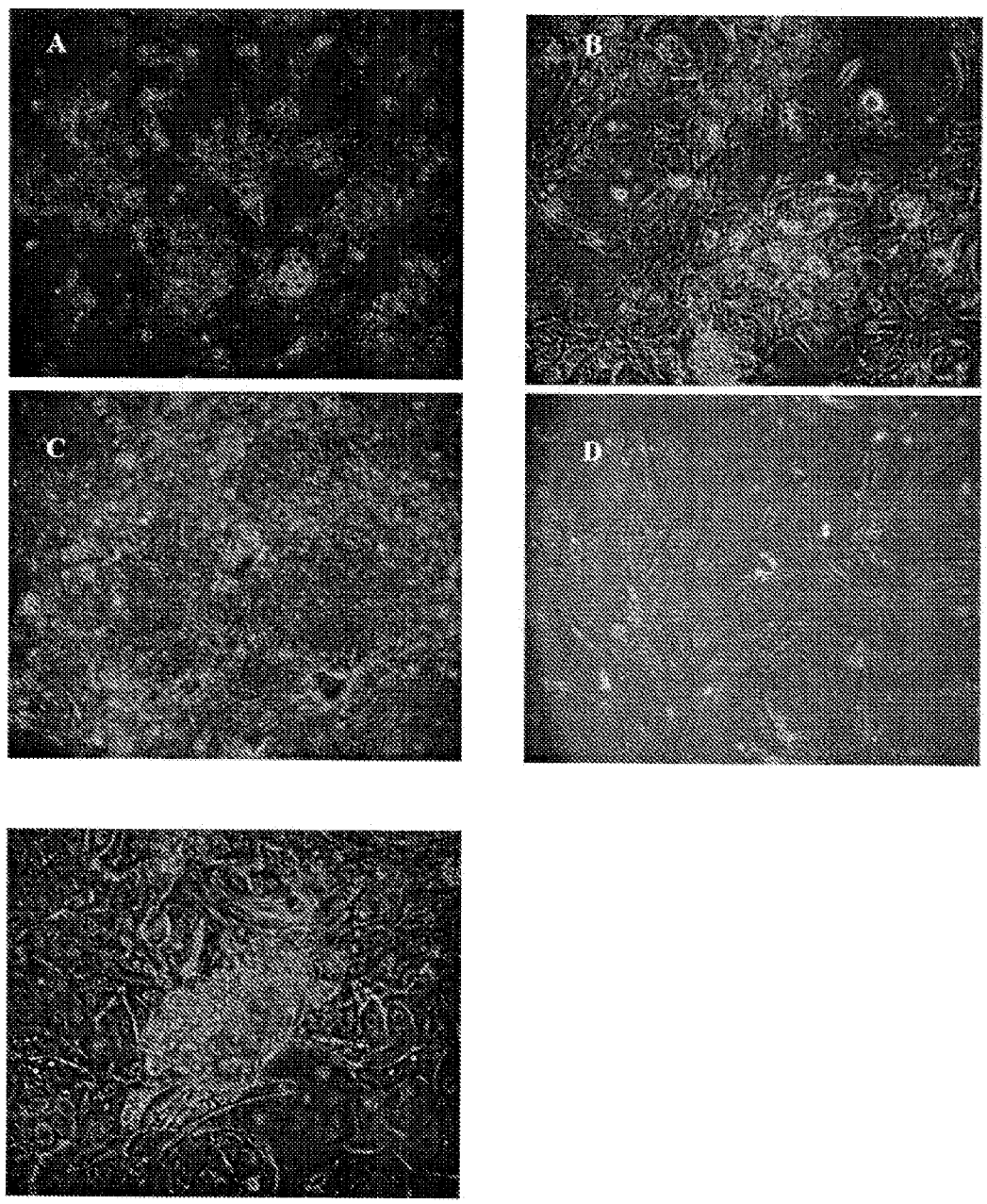
FIG. 3A shows a micrograph of a pancreatic ductal tissue fraction culture after six days of culture with HIP, (SEQ ID NO:2). New islet structure has formed within the cell culture.
FIG. 3B shows a micrograph of a pancreatic ductal tissue fraction culture after culture with HIP, (SEQ ID NO:2). New islet structure has formed within the cell culture.
FIG. 3C shows a micrograph of a pancreatic ductal tissue fraction culture after culture with HIP, (SEQ ID NO:2). New islet structure has formed within the cell culture.
FIG. 3D shows a micrograph of a pancreatic ductal tissue fraction culture without culture with HIP, (SEQ ID NO:2).
FIG. 3E shows a micrograph of a higher magnification micrograph of the micrograph shown in FIG. 3A.

Insulin levels were detected by Radioimmunoassay (RIA) from cultures treated with saline only, scrambled peptide, SEQ ID NOs: 7, 3 or 2 and hamster INGAP. The results for human ductal tissue fraction are shown in FIG. 1, and for human islet tissue in FIG. 2. Both fractions contain progenitor cells which are the nidus for new islet structures and upon which HIP exerts its stimulatory effect. FIG. 3 shows the ductal tissue culture fraction after HIP treatment, just before lysis and measurement by RIA. Morphological changes show islet like structure. Consistently we observe greater induction of new islets from the cells cultured from the ductal fraction of the pancreatic tissue. This observation is consistent with the notion that fewer progenitor cells are among the islet tissue fraction after the isolation process.

Example 2

HIP Induces Insulin Production In Vitro in Hud 270 Cells

Figure 4:
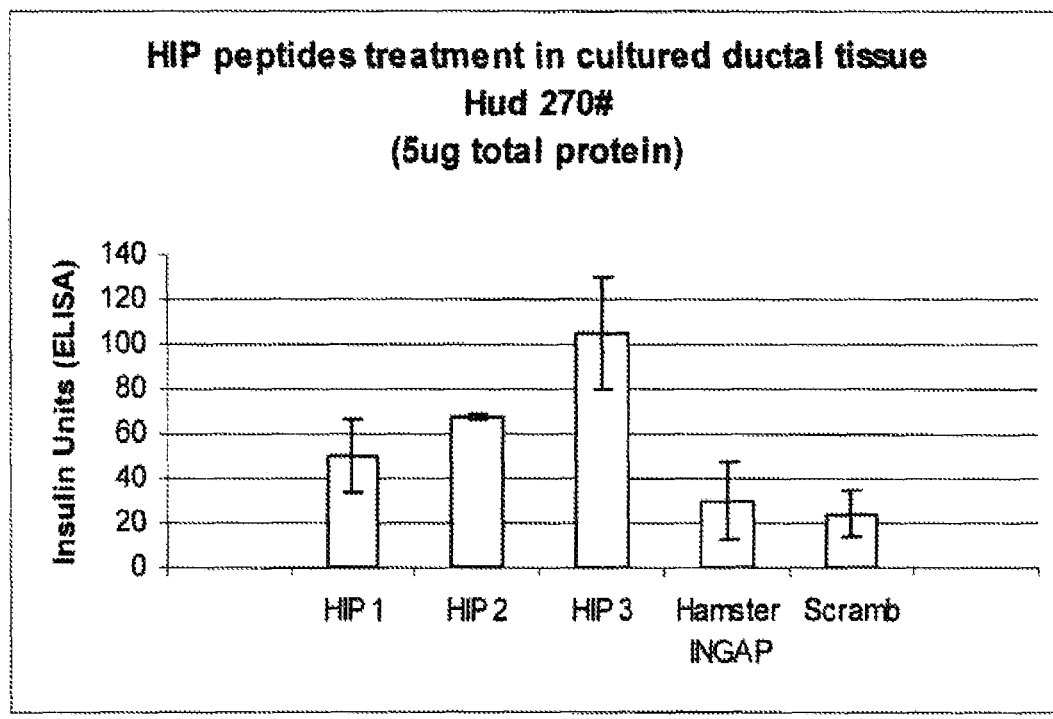
FIG. 4 is a bar graph showing increased insulin production in human pancreatic ductal tissue cultures treated with HIP peptides after 10 days according to Rosenberg protocol. Peptides 1, 2, 3 are HIP analogs SEQ ID 7, SEQ ID 3, and SEQ ID 2, as compared with similar treatment with Peptide 4 (the hamster INGAP sequence) and Peptide 5, a scrambled negative control. Samples are 5 µg total protein in duplicate and measured by ELISA assay.
Figure 5:
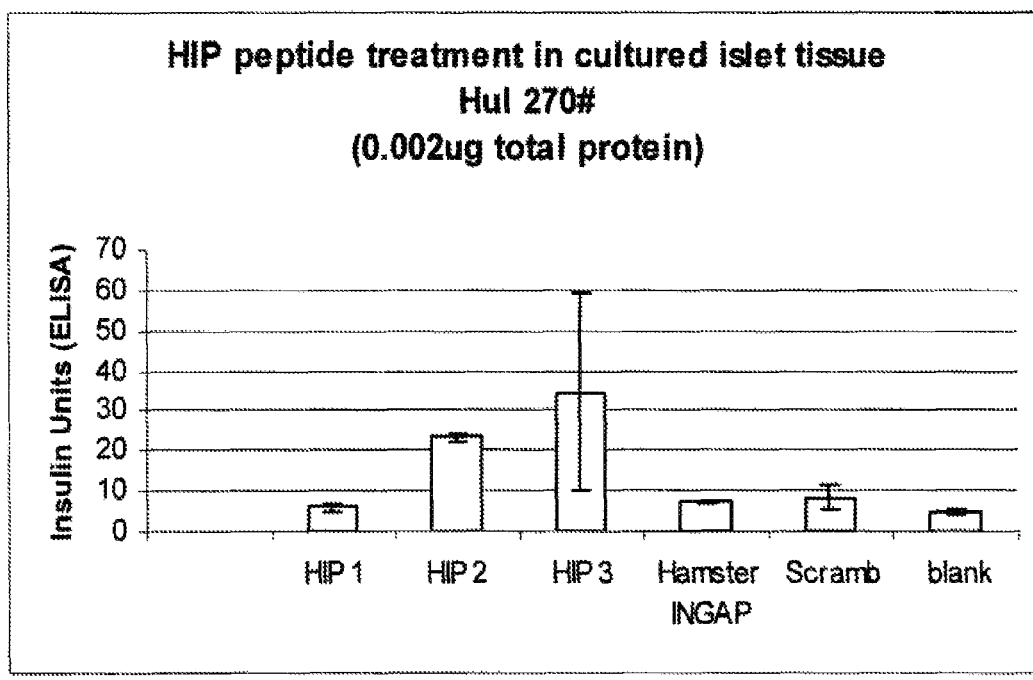
FIG. 5 is a bar graph showing increased insulin production in human pancreatic islet tissue cultures treated with HIP peptides after 10 days according to Rosenberg protocol. HIP1, 2 and 3 are HIP analogs SEQ ID NO:7, SEQ ID NO:3, and SEQ ID NO:2, as compared with similar treatment with Peptide 4 (the hamster INGAP sequence) and Peptide 5, a scrambled negative control. Samples 0.002 µg total protein in duplicate and measured by ELISA assay.
Figure 7:
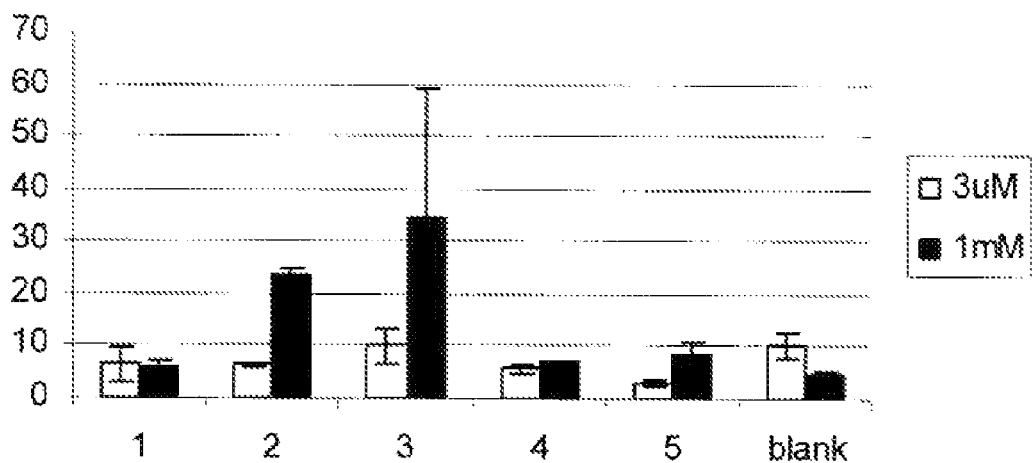
FIG. 7A is a bar graph showing increased insulin production in human pancreatic ductal tissue cultures treated with two concentrations of HIP peptides. HIP1, 2 and 3 are HIP analogs SEQ ID NO:7, SEQ ID NO:3, and SEQ ID NO:2, as compared with similar treatment with Peptide 4 (the hamster INGAP sequence) and Peptide 5, a scrambled negative control. Values are mean insulin units (of duplicate samples) as measured by ELISA assay.
FIG. 7B is a bar graph showing increased insulin production in human pancreatic islet tissue cultures treated with two concentrations of HIP peptides. HIP1, 2 and 3 are HIP analogs SEQ ID NO:7, SEQ ID NO:3, and SEQ ID NO:2, as compared with similar treatment with Peptide 4 (the hamster INGAP sequence) and Peptide 5, a scrambled negative control. Values are mean insulin units (of duplicate samples) as measured by ELISA assay.
Figure 7:
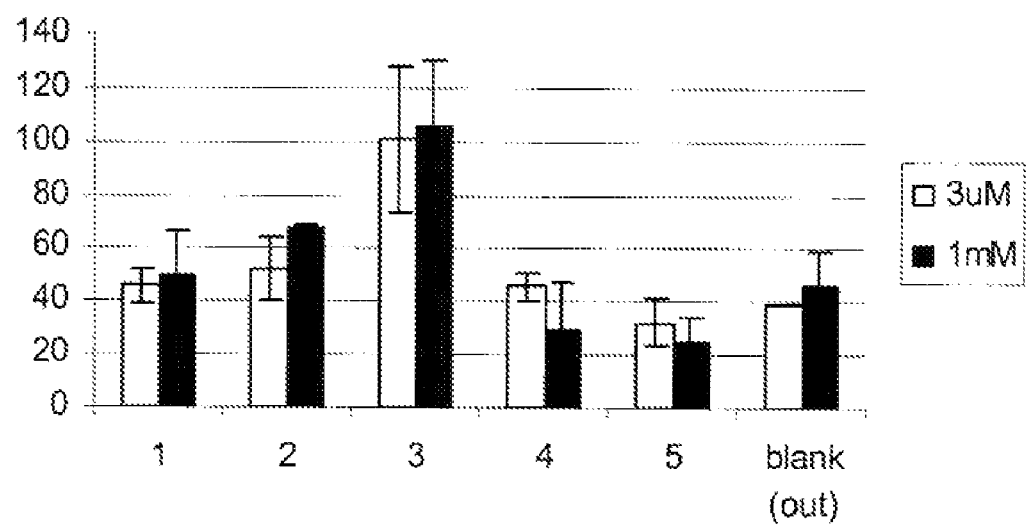

Human pancreatic tissue was treated as described in Example 1 and Insulin production was measured by ELISA assay. FIGS. 4 and 5 show the results of this experiment to show a dose response and to again compare the effect of HIP on the two different fractions of tissue as compared to the hamster INGAP sequence and a scrambled negative peptide sequence. Lanes 1-3 shows results from Hud 270 cells human ductal cells isolated as described in Example 1, treated with HIP with the sequences of SEQ ID NOs:7, 3 and 2, respectively. Lane 4 shows cells treated with a peptide with the INGAP sequence (SEQ ID NO:27). Lane 5 shows cells treated with a scrambled peptide (SEQ ID NO:28). The results in FIG. 4 involve the use of 5 µg of each peptide, while the results in FIG. 5 were acquired using 0.002 µg of each peptide. FIG. 7A shows results for cells cultured from the islet fraction and treated with 3 µM and 1 mM of each peptide, while FIG. 7B shows results for cells cultured from the ductal fraction and treated with 3 µM and 1 mM of each peptide.

Each of the HIP peptide sequences induced insulin production more effectively than INGAP or scrambled peptide, and the higher concentration of peptide produced a more profound effect in ductal cultures in which progenitor cells are more concentrated. In the islet cultures, the limiting factor for the degree to which the cultures are able to produce more insulin is not the concentration of the peptide, but the number of progenitor cells per culture.

Example 3

HIP Induces Islet Generation in Human Ductal Tissue Culture

Figure 6:
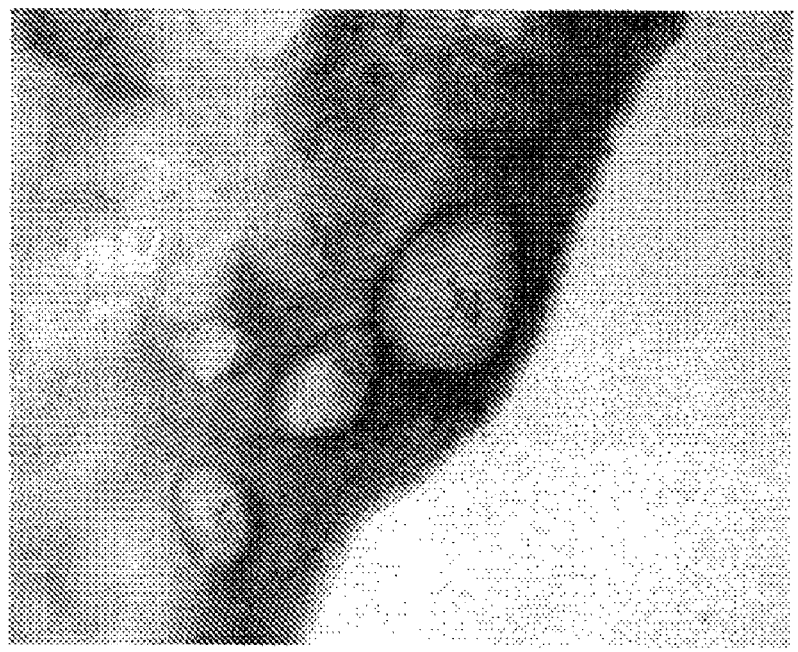
FIG. 6A is an inverted micrograph showing human pancreatic progenitor cells, forming a nidus of new insulin producing islets after two days of treatment with HIP.
FIG. 6B is an inverted micrograph showing human pancreatic progenitor cells forming insulin producing islet like structure after six days of treatment with HIP.
Figure 6:
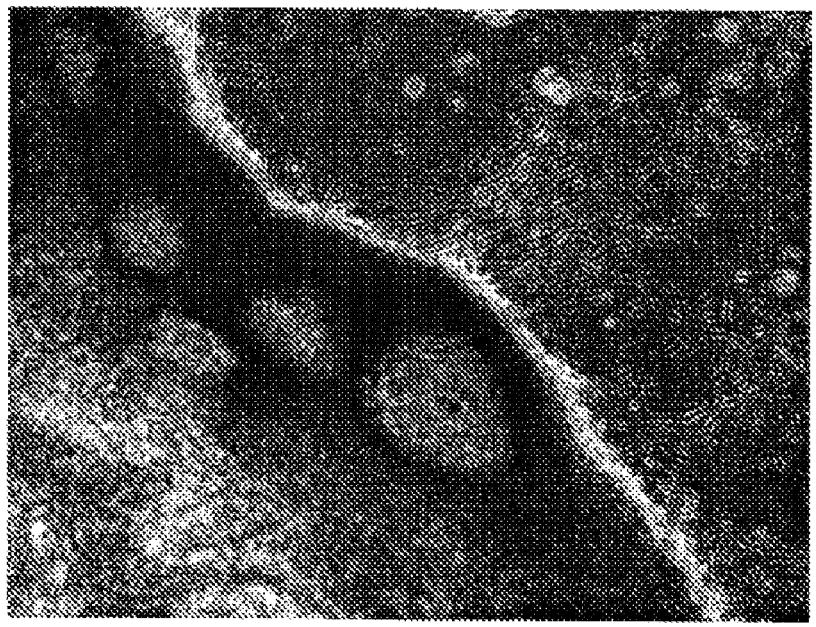

A human ductal tissue fraction was isolated and cultured as described in Example 1. After 10 days of culture, cells were treated with HIP for four days and observed using inverted microscopy. FIGS. 3A, 3B, and 3C shows cultures treated with HIP sequences, and 3D shows the negative control ductal tissue treated with no peptide. FIG. 6A shows human pancreatic progenitor tissue cultures at day 12 (day 2 of treatment with HIP). Islets have formed what has previously been described as ductal epithelial cysts and are starting to bud at one end where a progenitor cell resides. FIG. 7B shows human pancreatic progenitor tissue cultures at day 18 (day 6 of treatment with HIP). In this panel the darkening of the budding portion of the ductal epithelial cyst indicates the differentiation of cells consistent with previously shown changes that occur with hamster INGAP treatment in vitro.

Example 4

Clinical Trial Protocol for HIP

In this example, qualified animal models for diabetes are employed to examine the dose ranges of HIP.

Treatment with HIP

Animal Model. The non-obese diabetic (NOD) mouse strain has long been studied as an excellent model of type 1 diabetes because it spontaneously develops a disease that is very similar to the human condition. Delovitch, T. L., and Singh, B. 1997. *Immunity.* 7:727-738. Diabetes in NOD mice is mediated by inflammatory autoreactive T cells that recognize pancreatic islet antigens and escape central and peripheral tolerance.

Procedure: In a parental colony of NOD mice, incidence of diabetes in female NOD mice is typically 75-90% by 30 weeks but may exceed 90% in some cohorts. Each mouse receives dosages of HIP and is compared to NOD mice who does not receive HIP. Doses of HIP range from 1 µg/kg/day to 100 mg/kg/day.

Treatment. Cohorts are treated in 2 arms with 2-4 dose ranges of HIP and a placebo, at a compensated dose for animal size, metabolism and circulation, or about 1/6 the mg/kg equivalence. Arm 1: saline, Arm 2: HIP.

Study Assessment. Blood glucose levels are measured every week with a One Touch II glucose meter (Lifescan). Mice are considered diabetic after 2 consecutive measurements over 300 mg/dl. For histological analysis, pancreases are snap-frozen. Multiple 5-µm sections are stained with hematoxylin and eosin and scored blindly for severity of insulitis as known in the art.

Results. NOD mice taking HIP display a pronounced reduction in blood glucose levels and decreased showing of insulinitis in their pancreases.

Example 5

Clinical Trial Protocol to Examine Effects of HIP on Human Non-Endocrine Pancreatic Epithelial Cells A total of 48 adult NOD-scid mice will be used as recipients for transplants of tissue isolated from human pancreatic donor organs. Two cohorts will defined by the type of human tissue transplanted into the mice I) Nonendocrine ductal tissue and II) control nonpancreatic tissue.
Treatment of with HIP Peptides A total of 24 animals from each cohort will be randomized into one of 4 study groups for a total intervention of 39 days of twice daily intraperitoneal (IP) injections:
HIP Derivatives (250 µg/100 µl twice daily for a total of 500 µg/day)
  Blinded HIP A peptide SEQ ID NO:7 (n=6)
  Blinded HIP B peptide SEQ ID NO:3 (n=6)
  Blinded HIP C peptide SEQ ID NO:2 (n=6)
  Saline injected twice daily at an equivalent volume (100 µl) (n=6)

Blood glucose will be determined every three (3) days at the same time of day in all study animals. All animals will be killed on day 48 by exsanguination, and the transplant grafts will be will be excised for morphologic analysis.
Peptide Preparation Each vial contains 1500 µg of lyophilized HIP or analogues or derivatives thereof. Under sterile conditions, 600 µl isotonic saline will be added to each vial, providing six 100 µl IP sterile injections per vial for each study animal per group, one per animal each treatment time.
Glucose Measurements Plasma glucose measurements will be made on each animal in all study groups every three (3) days at the same time of day. Glucose levels over time will be evaluated for all study groups.
Human C-Peptide and Insulin Measurements Plasma and pancreatic insulin will be measured via a solid-phase radioimmunoassay. The collected blood will be centrifuged and the plasma frozen at −70° C. until assayed for insulin. A portion of each excised transplant will be weighed and then subjected to an overnight acid-ethanol extraction at 4° C. The cell-free extracts will be collected, neutralized with 0.4 M Tris base, and stored at −70° C. until being assayed for human C-peptide and insulin. Determinations will be performed in triplicate.
Microscopy and Morphometric Analysis On excision of human tissue, each will be weighed and then fixed in paraformaldehyde. Embedded samples will be stained and evaluated for
  a) islet number/mm$^2$,
  b) beta cell mass/mg tissue weight,
  c) duct associated and extra-islet acinar-associated beta cell mass, and
  d) percentage of PDX-1 immunopositive duct cells.

Tissue will be probed with primary antibodies directed against human C-peptide, human insulin, human glucagon, human somatostatin and human pancreatic polypeptide.

Example 6

Clinical Trial Protocol for HIP and GLP-1 or GLP-1 Receptor Agonist, GLP-1 Analog In this example, qualified animal models for diabetes are employed to examine the dose ranges of synergistic interaction of HIP and agents for stimulating pancreatic islet cell regeneration.
Treatment with HIP and GLP-1 or GLP-1 Receptor Agonist or GLP-1 Analog Animal Model. The non-obese diabetic (NOD) mouse strain has long been studied as an excellent model of type 1 diabetes because it spontaneously develops a disease that is very similar to the human condition. Delovitch, T. L., and Singh, B. 1997. *Immunity*. 7:727-738. Diabetes in NOD mice is mediated by inflammatory autoreactive T cells that recognize pancreatic islet antigens and escape central and peripheral tolerance.

Procedure: In a parental colony of NOD mice, incidence of diabetes in female NOD mice is typically 75-90% by 30 weeks but may exceed 90% in some cohorts. Each mouse receives dosages of HIP and/or amylin and is compared to NOD mice that receive neither. Doses of HIP range from 1 µg/kg/day to 100 mg/kg/day. Doses of amylin range from 0.3-0.8 µg/kg/day.

Treatment. Cohorts are treated in 4 arms with 2-4 dose ranges of each drug and a placebo, at a compensated dose for animal size, metabolism and circulation, or about 1/6 the mg/kg equivalence. Arm 1: saline, Arm 2: HIP; Arm 3: amylin; Arm 4: HIP plus amylin.

Study Assessment. Blood glucose levels are measured every week with a One Touch II glucose meter (Lifescan). Mice are considered diabetic after 2 consecutive measurements over 300 mg/dl. For histological analysis, pancreases are snap-frozen. Multiple 5-µm sections are stained with hematoxylin and eosin and scored blindly for severity of insulitis as known in the art.

Results. NOD mice taking HIP display a pronounced reduction in blood glucose levels and decreased showing of insulinitis in their pancreases.

Example 7

Clinical Trial Protocol for HIP, Amylin/SYMLIN™ and DIAPEP277™ in Patients with Preexisting Type 1 Diabetes In this example for the human clinical trial, the 5 step method to be utilized among type 1 patients is outlined utilizing HIP, SYMLIN™ and DIAPEP277™. The five step methods for treatment of type 1 diabetes with HIP and/or HIP analogs includes the following steps: 1) Intensive Glycemic Management, 2) Achievement and maintenance of 25-hyrdroxyvitamin D levels to >40 ng/dl via oral cholecalciferol (Vitamin D3) 3) Immune Therapy, 4) HIP administration and Insulin tapering followed by discontinuation of both HIP and Insulin and 5) Immune modulation protocol with DiaPep277 at the end of month 2 of the intensification of glucose, and at the onset up usage of HIP and at 6 months following the initiation of HIP (Raz et al., Lancet. 2001:24; 358(9295):1749-53) and as necessary based upon C-peptide and GAD antibody titers.

Qualified patients with type 1 diabetes will be selected for study and all patients will receive 3 months of intensification of their diabetes with multiple insulin injections, insulin pump usage and/or addition of SYMLIN™ prior to meals with an appropriate reduction in pre-meal insulin. During this period of intensive glucose management, all patients will have their 25-hydroxyvitamin D measured, and those patients with values less than 40 ng/ml will have 1000 or 2000 IU Vitamin D3 (cholecalciferol) added to their treatment regiment.

Half of the patients will be randomized to the intervention group or placebo group. The placebo group will receive one placebo/vehicle subcutaneous injection at the end of month two of intensification of glucose vs. those in the intervention trial, who will receive a subcutaneous injection of 1 mg of subcutaneous DIAPEP277™ (Raz et al., Lancet. 2001:24; 358(9295):1749-53). Patients will be seen weekly and modifications made in their diabetes regimen.

At the end of three months of intensification, patients in both groups will continue to have 25-hydroxy vitamin D levels measured and maintenance of Vitamin D3 as necessary to ensure levels above 40 ng/ml. Those patients in the intervention arm, will receive another subcutaneous injection of DIAPEP277™, while the placebo arm will receive a placebo/vehicle injection. Those patients on insulin and SYMLIN™ or insulin alone, who are randomized to HIP therapy, dosed at a total of 800-900 mg/day (average dosage of 10 mg/kg/day in 4 divided dosages) given in subcutaneous injections prior to each meal and at bedtime. Those in the placebo group will take 4 injections of an inert vehicle before meals and at bedtime.

All patients will be monitored closely, with glucose levels, C-peptide and stimulated C-peptide levels. Insulin and SYMLIN™ will be titrated as necessary to maintain goal glucose levels of 80-110 mg/dL fasting and 110-140 mg/dL two hours post-prandially. Within 3-6 months, it is expected that the intervention group may be completely tapered off insulin. At the end of 6 months following the initial administration HIP or placebo therapy, a final injection of DIAPEP277™ or placebo will be given to protect new islets in the intervention group.

Example 8

Clinical Trial Protocol for HIP, Amylin/SYMLIN™ and DIAPEP277™ in Patients with New Onset Type 1 Diabetes In this example for the human clinical trial, methods to be utilized among type 1 patients is outlined utilizing HIP, SYMLIN™ and DIAPEP277™. The methods for treatment of type 1 diabetes with HIP and/or HIP analogs includes the following steps: 1) Immediate randomization to intervention or control group followed by administration of DIAPEP277™ subcutaneously vs. placebo among control patients 2) Achievement and maintenance of 25-hyrdroxyvitamin D levels to >40 ng/dl via oral cholecalciferol (Vitamin D3) 3) One month intensive management with Insulin and SYMLIN™ 4) HIP administration and Insulin tapering followed by discontinuation of both HIP and Insulin and 5) Immune modulation protocol with DiaPep277 at one month following the initial injection then again at 6 months (Raz et al., Lancet. 2001:24; 358(9295):1749-53) and as necessary based upon C-peptide and GAD antibody titers.

Qualified patients with new onset type 1 diabetes will be selected for study and all patients will receive either placebo or DIAPEP277™ followed by 1 months of intensification of their diabetes with multiple insulin injections, insulin pump usage and/or addition of SYMLIN™ prior to meals with an appropriate reduction in premeal insulin. During this period of intensive glucose management, all patients will have their 25-hydroxyvitamin D measured, and those patients with values less than 40 ng/ml will have 1000 or 2000 IU Vitamin D3 (cholecalciferol) added to their treatment regiment.

At the end of one months of intensification, patients in both groups will continue to have 25-hydroxy vitamin D levels measured and maintenance of Vitamin D3 as necessary to ensure levels above 40 ng/ml. Those patients in the intervention arm, will receive another subcutaneous injection of DIAPEP277™, while the placebo arm will receive a placebo/vehicle injection. Those patients on insulin and SYMLIN™ or insulin alone, who are randomized to HIP therapy, dosed at a total of 800-900 mg/day (average dosage of 10 mg/kg/day in 4 divided dosages) given in subcutaneous injections prior to each meal and at bedtime. Those in the placebo group will take 4 injections of an inert vehicle before meals and at bedtime.

All patients will be monitored closely, with glucose levels, C-peptide and stimulated C-peptide levels. Insulin and SYMLIN™ will be titrated as necessary to maintain goal glucose levels of 80-110 mg/dL fasting and 110-140 mg/dL two hours post-prandially. Within 3-6 months, it is expected that the intervention group may be completely tapered off insulin. At the end of 6 months following the initial administration HIP or placebo therapy, a final injection of DIAPEP277™ or placebo will be given to protect new islets in the intervention group.

Animal Model. The non-obese diabetic (NOD) mouse strain has long been studied as an excellent model of type 1 diabetes because it spontaneously develops a disease that is very similar to the human condition. Delovitch, T. L., and Singh, B. 1997. Immunity. 7:727-738. Diabetes in NOD mice is mediated by inflammatory autoreactive T cells that recognize pancreatic islet antigens and escape central and peripheral tolerance.

Procedure: In a parental colony of NOD mice, incidence of diabetes in female NOD mice is typically 75-90% by 30 weeks but may exceed 90% in some cohorts. Each mouse receives dosages of HIP and/or amylin and/or DIAPEP277™ and is compared to each other and NOD mice who receive nothing. Doses of HIP range from 1 µg/kg/day to 100 mg/kg/day. Doses of amylin range from 0.3-0.8 µg/kg/day. Doses of DIAPEP277™ range from about 0.1-0.2 mg 1 week before the administration of HIP or amylin.

Treatment. Cohorts are treated in 6 arms with 2-4 dose ranges of each drug and a placebo, at a compensated dose for animal size, metabolism and circulation, or about 1/6 the mg/kg equivalence. Arm 1: saline, Arm 2: HIP; Arm 3: amylin; Arm 4: HIP plus amylin; Arm 5 HIP plus DIAPEP277™; Arm 6 HIP plus amylin plus DIAPEP277™.

Study Assessment. Blood glucose levels are measured every week with a One Touch II glucose meter (Lifescan).

Mice are considered diabetic after 2 consecutive measurements over 300 mg/dl. For histological analysis, pancreases are snap-frozen. Multiple 5-μm sections are stained with hematoxylin and eosin and scored blindly for severity of insulitis as known in the art.

Results. NOD mice taking HIP display a pronounced reduction in blood glucose levels and decreased showing of insulinitis in their pancreases.

Although the present invention has been described in detail with reference to specific embodiments, those of skill in the art will recognize that modifications and improvements are within the scope and spirit of the invention, as set forth in the claims which follow. All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

We claim:

1. A method of treating type 1 diabetes in a mammalian subject comprising administering to said subject a human proislet peptide consisting of the amino acid sequence SEQ ID NO. 7.

2. The method of claim 1 further comprising the step of administering one or more agents for stimulating pancreatic islet cell regeneration.

3. The method of claim 2, wherein the agent for stimulating pancreatic islet cell regeneration is selected from a member of the group consisting of human proislet peptide, amylin, pramlinitide, exendin-4, liraglutide, GLP-1 receptor agonists, GLP-1, hamster INGAP, GIP, dipeptydyl peptidase-4 inhibitors and analogs thereof.

4. The method of claim 1 further comprising the step of administering one or more agents that inhibit autoimmune cells that target pancreatic islet cells.

5. The method of claim 4, wherein the agent that inhibits the autoimmune cells that target pancreatic islet cells is selected from the group consisting of anti-CD3 antibody, rapamycin, FK506, heat-shock protein, tacrolimus, GAD65 vaccine, mycophenolate mofetil, lysofylline, rituximab, daclizumab, anti-CD52 antibody, anti-CD20 antibody, Vitamin D, IBC-VSO vaccine, interferon alpha and $CD4^+CD25^+$ antigen-specific regulatory T cells.

6. The method of claim 5, wherein the mycophenolate mofetil is coadministered with daclizumab.

7. The method of claim 5, wherein the vitamin D is vitamin D3.

8. The method of claim 7, wherein the vitamin D3 is administered in an amount effective to maintain 25-hydroxy vitamin D above about 40 ng/mL.

9. The method of claim 1, wherein at least one symptom of type 1 diabetes is treated as a result of the administration of the peptide.

10. The method of claim 9, wherein the symptom is selected from a member of the group consisting of frequent urination, excessive thirst, extreme hunger, unusual weight loss, increased fatigue, irritability, blurry vision, genital itching, odd aches and pains, dry mouth, dry or itchy skin, impotence, vaginal yeast infections, poor healing of cuts and scrapes, excessive or unusual infections, hyperglycemia, loss of glycemic control, fluctuations in postprandial blood glucose, fluctuations in blood glucagons and fluctuations in blood triglycerides.

11. The method of claim 1, wherein the mammal is selected from a human, a horse, a cow, a sheep, a dog and a cat.

12. The method of claim 1, wherein the peptide is administered in a pharmaceutical composition.

13. The method of claim 1, wherein the peptide is administered by a route selected from orally, subcutaneously, transdermally, intranasally, parenterally, topically and buccally.

14. The method of claim 1 further comprising administering insulin.

15. The method of claim 14, wherein the insulin is diminished in dosage after the administration of the human proislet peptide.

16. The method of claim 15, wherein the insulin dosage is diminished one or more times after the administration of the human proislet peptide.

17. The method of claim 16, wherein the insulin dosage is diminished to zero.

18. The method of claim 1, wherein said human proislet peptide is conjugated to a compound selected from albumin, transferrin and polyethylene glycol.

19. The method of claim 1, further comprising the step of intensifying glycemic control prior to administration of the human proislet peptide.

20. A kit for treating a patient having pre-diabetes, type 2 diabetes or latent autoimmune diabetes comprising a therapeutically effective dose of a human proislet peptide consisting of the amino acid sequence SEQ ID NO. 7, at least one agent for stimulating pancreatic islet cell regeneration and instructions for its use.

* * * * *